US012027250B2

(12) United States Patent
Shiraga

(10) Patent No.: US 12,027,250 B2
(45) Date of Patent: Jul. 2, 2024

(54) MEDICAL INFORMATION PROCESSING APPARATUS AND INFORMATION PROCESSING METHOD

(71) Applicant: Sony Olympus Medical Solutions Inc., Tokyo (JP)

(72) Inventor: Mitsuaki Shiraga, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 168 days.

(21) Appl. No.: 16/768,081

(22) PCT Filed: Oct. 2, 2018

(86) PCT No.: PCT/JP2018/036760
§ 371 (c)(1),
(2) Date: May 29, 2020

(87) PCT Pub. No.: WO2019/111512
PCT Pub. Date: Jun. 13, 2019

(65) Prior Publication Data
US 2020/0312464 A1 Oct. 1, 2020

(30) Foreign Application Priority Data
Dec. 5, 2017 (JP) .................................. 2017-233379

(51) Int. Cl.
*G16H 20/40* (2018.01)
*A61B 1/00* (2006.01)
(Continued)

(52) U.S. Cl.
CPC ......... *G16H 20/40* (2018.01); *A61B 1/00009* (2013.01); *A61B 5/02042* (2013.01);
(Continued)

(58) Field of Classification Search
CPC . A61B 90/37; A61B 1/00009; A61B 5/02042; G16H 40/67; G16H 15/00;
(Continued)

(56) References Cited

U.S. PATENT DOCUMENTS 9,788,907 B1 10/2017 Alvi et al.
2003/0216836 A1 11/2003 Treat et al.
(Continued)

FOREIGN PATENT DOCUMENTS

JP 3104051 U 6/2004
JP 2006-43209 A 2/2006
(Continued)

OTHER PUBLICATIONS

Kenji Suzuki, Overview of deep learning in medical imaging, 10 Radiological Physics and Technology 257-273 (Jul. 8, 2017) (Year: 2017).*

(Continued)

*Primary Examiner* — Jordan L Jackson
(74) *Attorney, Agent, or Firm* — XSENSUS LLP

(57) ABSTRACT

The present disclosure provides a medical information processing apparatus that comprises: a selection unit that selects, from among candidate data including surgery data acquired during surgery, target data corresponding to selection conditions that include a condition relating to a patient attribute, a condition relating to a surgical-procedure type, and a condition relating to a disease type; an extraction unit that detects a feature from the selected target data and extracts, from the target data, feature data corresponding to the detected feature; and an editing processing unit that edits the extracted feature data, wherein the extraction unit extracts at least a medical image as the feature data.

20 Claims, 15 Drawing Sheets

(51) Int. Cl.
| | |
|---|---|
| *A61B 5/02* | (2006.01) |
| *A61B 90/00* | (2016.01) |
| *A61M 16/01* | (2006.01) |
| *B25J 9/16* | (2006.01) |
| *G05B 13/02* | (2006.01) |
| *G16H 15/00* | (2018.01) |
| *G16H 30/20* | (2018.01) |
| *G16H 30/40* | (2018.01) |
| *G16H 40/67* | (2018.01) |
| *G16H 50/20* | (2018.01) |
| *G16H 50/70* | (2018.01) |
| *G16H 70/20* | (2018.01) |

(52) U.S. Cl.
CPC .............. *A61B 90/37* (2016.02); *A61M 16/01* (2013.01); *B25J 9/1697* (2013.01); *G05B 13/0265* (2013.01); *G16H 15/00* (2018.01); *G16H 30/20* (2018.01); *G16H 30/40* (2018.01); *G16H 40/67* (2018.01); *G16H 50/20* (2018.01); *G16H 50/70* (2018.01); *G16H 70/20* (2018.01); *G05B 2219/45117* (2013.01)

(58) Field of Classification Search
CPC ........ G16H 30/20; G16H 50/20; G16H 30/40; G16H 70/20; G16H 50/70; A61M 16/01; B25J 9/1697; G05B 13/0265; G05B 2219/45117
See application file for complete search history.

(56) References Cited

U.S. PATENT DOCUMENTS

| | | | | |
|---|---|---|---|---|
| 2009/0088634 | A1* | 4/2009 | Zhao | G06V 20/00 600/425 |
| 2010/0198402 | A1* | 8/2010 | Greer | A61B 90/11 700/247 |
| 2011/0046476 | A1 | 2/2011 | Cinquin et al. | |
| 2012/0183191 | A1* | 7/2012 | Nakamura | A61B 5/416 382/128 |
| 2014/0185888 | A1* | 7/2014 | Kelm | G06K 9/6282 382/128 |
| 2014/0287393 | A1* | 9/2014 | Kumar | G09B 5/02 434/262 |
| 2014/0343586 | A1* | 11/2014 | Sakuragi | A61B 5/0033 606/167 |
| 2016/0278870 | A1* | 9/2016 | Quaid | A61N 1/3605 |
| 2016/0381256 | A1* | 12/2016 | Aguirre-Valencia | H04N 13/30 348/46 |
| 2017/0143284 | A1* | 5/2017 | Sehnert | A61B 6/5258 |
| 2017/0151027 | A1* | 6/2017 | Walker | A61B 34/25 |
| 2017/0345155 | A1* | 11/2017 | Higgins | G06T 7/162 |
| 2018/0065248 | A1* | 3/2018 | Barral | G16H 50/50 |
| 2018/0137244 | A1* | 5/2018 | Sorenson | G16H 30/20 |
| 2018/0233222 | A1* | 8/2018 | Daley | G16H 50/50 |
| 2019/0046813 | A1* | 2/2019 | Zhou | G16H 50/70 |
| 2019/0133693 | A1* | 5/2019 | Mahfouz | G06T 17/00 |

FOREIGN PATENT DOCUMENTS

| | | |
|---|---|---|
| JP | 2011-167301 A | 9/2011 |
| JP | 2016-42982 A | 4/2016 |
| JP | 2016-154810 A | 9/2016 |
| JP | 2017-47022 A | 3/2017 |
| WO | 2006/077798 A1 | 7/2006 |
| WO | 2016/200887 A1 | 12/2016 |
| WO | 2017/083768 A1 | 5/2017 |

OTHER PUBLICATIONS

Geert Litjens et al., Deep Learning Applications in Medical Image Analysis, 42 Medical Image Analysis 60-88 (Jul. 26, 2017) (Year: 2017).*

Shugiong Wu et al., Continuous lung region segmentation from endoscopic images for intra-operative navigation, 87 Computers in Biology and Medicine 200-210 (Aug. 1, 2017) (Year: 2017).*

Michael S. Block et al., Implant Placement Is More Accurate Using Dynamic Navigation, 75(7) J of Oral and Maxillofacial Surgery 1377-1386 (Jul. 2017) (Year: 2017).*

Constantinos Loukas, "Video content analysis of surgical procedures", Surgical Endoscopy, 2018, vol. 32, No. 2, pp. 553-568, DOI:10.1007/S00464-017-5878-1, Springer, Published online: Oct. 26, 2017, XP036393146, ISSN:0930-2794 [retrieved on Oct. 26, 2017].

Bernd Münzer et al., "Content-based processing and analysis of endoscopic images and videos: A survey", Multimed Tools Appl, 2018, vol. 77, No. 1, pp. 1323-1362, DOI 10.1007/s11042-016-4219-z, Springer, Published online: Jan. 11, 2017, XP036403706, ISSN:1380-7501 [retrieved on Jan. 11, 2017].

Extended European search report dated Aug. 10, 2020, in corresponding European patent Application No. 18886892.1, 10 pages.

International Search Report and Written Opinion dated Jan. 30, 2019 for PCT/JP2018/036760 filed on Oct. 2, 2018, 8 pages including English Translation of the International Search Report.

Ohnuma. K., et al., "Intraoperative Analysis of Surgeon's Motions and Construction of Timed Automata Based Model of Laparoscopic Surgery for Human-adaptive Surgical Robot System," Transactions of the Society of Instrument and Control Engineers, vol. 43, No. 8, 2007, pp. 679-688 (with English Abstract).

* cited by examiner

MEDICAL INFORMATION PROCESSING APPARATUS AND INFORMATION PROCESSING METHOD

CROSS-REFERENCE TO RELATED APPLICATIONS

The present application is based on PCT filing PCT/JP2018/036760, filed Oct. 2, 2018, which claims priority to JP 2017-233379, filed Dec. 5, 2017, the entire contents of each are incorporated herein by reference.

TECHNICAL FIELD

The present disclosure relates to a medical information processing apparatus and an information processing method.

BACKGROUND ART

In surgery, various data generated by various surgery-related devices (hereinafter may be referred to as "surgery data" collectively or to denote individual data items) is recorded on a recording medium. Under these circumstances, techniques for efficiently managing surgery data have been developed. Techniques for efficiently managing surgery data include the technique disclosed in Patent Literature 1 below, for example.

Furthermore, techniques for analyzing endoscope images obtained by an endoscope have been developed. The technique disclosed in Patent Literature 2 below, for example, may be cited as "a technique for establishing categories corresponding to pathologic diagnoses by using results obtained by extracting cell nuclei contained in an endoscope image to measure features and using results obtained by performing texture analysis on the whole endoscope image".

CITATION LIST

Patent Literatures

Patent Literature 1: WO 2006/077798 A
Patent Literature 2: JP 2016-154810 A

DISCLOSURE OF INVENTION

Technical Problem

As mentioned earlier, surgery data is generated by various devices in surgery, and the surgery data is recorded on a recording medium. For example, in a case where a health worker such as a physician is attempting to make secondary use of surgery data stored on a recording medium, the health worker needs to perform an enormous amount of work in which the health worker "reproduces all the surgery data and uses editing software or the like to crop a snapshot" and "compiles surgery data and medical illustration images such as autopsy diagrams to create a workflow for a case surgery protocol", and so forth.

The present disclosure proposes a new and improved medical information processing apparatus and information processing method which enable improvements in health worker convenience.

Solution to Problem according to the present disclosure, there is provided a medical information processing apparatus including: a selection unit that selects, from among candidate data including surgery data acquired during surgery, target data corresponding to selection conditions that include a condition relating to a patient attribute, a condition relating to a surgical-procedure type, and a condition relating to a disease type; an extraction unit that detects a feature from the selected target data and extracts, from the target data, feature data corresponding to the detected feature; and an editing processing unit that edits the extracted feature data, wherein the extraction unit extracts at least a medical image as the feature data.

Moreover, according to the present disclosure, there provided an information processing method executed by a medical information processing apparatus, the method including the steps of: selecting, from among candidate data including surgery data acquired during surgery, target data corresponding to selection conditions that include a condition relating to a patient attribute, a condition relating to a surgical-procedure type, and a condition relating to a disease type; detecting a feature from the selected target data and extracting, from the target data, feature data corresponding to the detected feature; and editing the extracted feature data, wherein, in the extraction step, at least a medical image is extracted as the feature data.

Advantageous Effects of Invention

According to the present disclosure, improvements in health worker convenience are enabled.

Note that the foregoing advantageous effects are not necessarily limited, rather, any advantageous effects disclosed in the present specification or other advantageous effects which can be ascertained from the present specification may be included in addition to the foregoing advantageous effects or instead of the foregoing advantageous effects.

BEST MODE FOR CARRYING OUT THE INVENTION

Preferred embodiments of the present disclosure will be described in detail hereinbelow with reference to the accompanying drawings. Note that duplicate descriptions are omitted from the present specification and drawings by assigning the same reference signs to constituent elements which have substantially the same function configurations.

In addition, the description will be provided hereinbelow in the following order:

1. Information processing method according to the present embodiment
2. Medical information processing apparatus according to the present embodiment
3. Programs according to the present embodiment (Information Processing Method According to the Present Embodiment)

An example of a case where the medical information processing apparatus according to the present embodiment performs processing pertaining to the information processing method according to the present embodiment is provided hereinbelow. Furthermore, processing pertaining to the information processing method according to the present embodiment will be described hereinbelow after describing "an example of the medical information processing system according to the present embodiment that includes the medical information processing apparatus according to the present embodiment".

[1] Configuration of Medical Information Processing System

Figure 1:
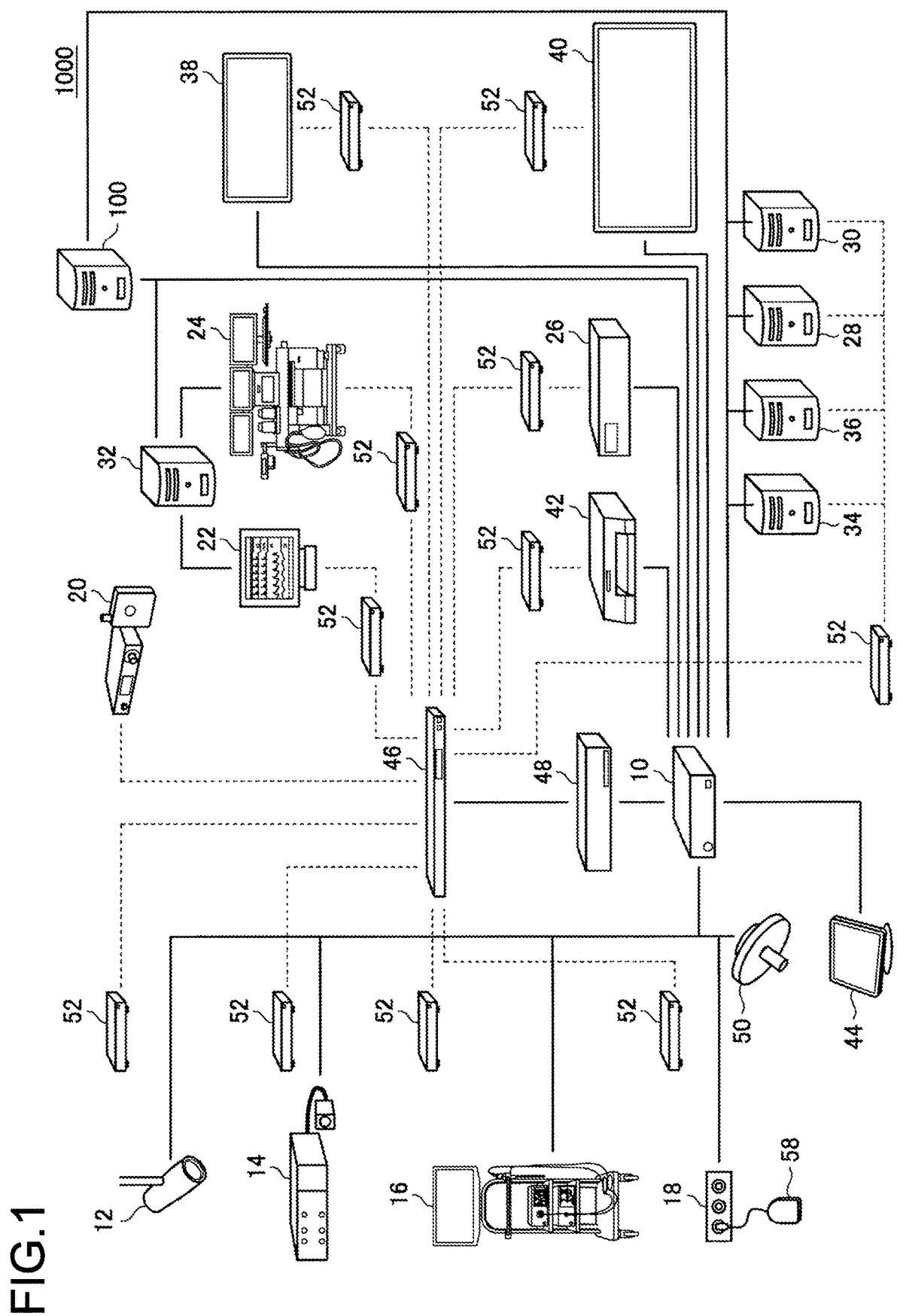
FIG. 1 is an explanatory drawing illustrating an example of a configuration of a medical information processing system according to the present embodiment.

FIG. 1 is an explanatory drawing illustrating an example of the configuration of a medical information processing system 1000 according to the present embodiment. In FIG. 1, the flow of data representing images and/or sound among the surgery data is denoted by dashed lines. Further, in FIG. 1, the flow of data other than the data representing images and/or sound (for example, other surgery data or data pertaining to device control, and the like) is denoted by solid lines.

The medical information processing system 1000 includes a medical information processing apparatus 100 according to the present embodiment. An example of the configuration of the medical information processing apparatus 100 and an example of processing by the medical information processing apparatus 100 (processing pertaining to the information processing method according to the present embodiment) will be described subsequently.

In addition, the medical information processing system 1000 includes, for example, a medical controller 10, an acquiring device, a storage device, a patient information management device, a data output device, an operating device, and a switcher 46. Each of the devices constituting the medical information processing system 1000 are driven by electrical power supplied from an internal power supply such as a battery which each device comprises or by electrical power supplied from an external power supply connected to each device, or the like.

Acquiring devices of the medical information processing system 1000 are devices that acquire various surgery data. Acquiring devices include, for example, an overhead camera 12, a surgical area camera 14, an endoscope/medical apparatus 16, an external input terminal 18, an intercom 20, a biometric monitor 22, and an anesthesia system 24.

Storage devices of the medical information processing system 1000 are devices that store acquired surgery data. Storage devices include, for example, a recorder 26, a moving image server 28, a device log data server 30, and an anesthesiology server 32.

Patient information management devices of the medical information processing system 1000 are devices that manage patient information constituting data on patients. Patient information management devices include, for example, an electronic medical record server 34 and a DICOM (Digital Imaging and COmmunication in Medicine) server 36.

Patient information includes the data (or data sets) listed below, for example. It goes without saying that examples of patient information are not limited to or by the examples below. All or part of the data constituting patient information corresponds to the electronic medical record information (described subsequently) which is stored on the electronic medical record server 34.

Identification data uniquely identifying a patient (an ID identifying a patient, for example)
Data indicating a procedure applied to surgery performed on a patient
Data indicating the gender of a patient
Data indicating the age range (or age) of a patient
Patient biometric data
Data indicating a type of disease
Data indicating the medical history of a patient
Data indicating the surgical history of a patient
Data indicating the medication history of a patient
Patient examination data
Postoperative data relating to the patient after surgery (for example, data indicating QALI (Quality Adjusted Life Years), data indicating QOL (Quality Of Life), data indicating the number of days after discharge, and data indicating the existence and type of complications, and so forth).
Combinations of two or more of the data above Data output devices of the medical information processing system 1000 are devices that output acquired surgery data and/or patient information. Data output devices include, for example, a ceiling-mounted monitor 38, a wall monitor 40, and a printer 42, for example. Note that the data output devices are not limited to or by the foregoing examples. For example, a data output device may also be any mobile device such as a tablet-type device or a portable computer.

An operating device of the medical information processing system 1000 is a device that enables the person using the operating device to perform an operation.

Various equipment constituting the medical information processing system 1000 such as the medical controller 10, for example, are operated by operating an operating device. Operating devices for operating the medical controller 10 include a touch panel 44, for example.

Note that operating devices of the medical information processing system 1000 are not limited to devices with which equipment is operated. For example, an operating device of the medical information processing system 1000 may generate text data in cases where text (character strings or documents, for example) is input by operating the operating device.

The switcher 46 of the medical information processing system 1000 is a device for controlling the input/output, to/from each device, of various acquired data such as surgery data.

Among the devices constituting the medical information processing system 1000, the acquiring devices, the data output devices and the operating devices, for example, are installed in the operating room. Furthermore, among the devices constituting the medical information processing system 1000, the medical controller 10, storage devices, patient information management devices, the switcher 46, and the medical information processing apparatus 100 are installed outside the operating room and in optional positions inside or outside the hospital, for example. It goes without saying that examples of where the respective devices constituting the medical information processing system 1000 are disposed are not limited to or by the foregoing examples.

Among the devices constituting the medical information processing system 1000, the devices other than the medical information processing apparatus 100, described subsequently, will be described in more specific terms hereinbelow.

[1-1] Medical Controller 10

The medical controller 10 is communicably connected to the respective devices constituting the medical information processing system 1000 and controls the action of each device. Note that, in the example illustrated in FIG. 1, the medical controller 10 is not connected to the intercom 20, the biometric monitor 22, or the anesthesia system 24. Hence, in the example illustrated in FIG. 1, the intercom 20, biometric monitor 22, and anesthesia system 24 are each capable of functioning independently of the medical controller 10.

More specifically, the medical controller 10 controls the action of the acquiring devices to cause same to acquire surgery data.

Furthermore, the medical controller 10 controls the action of the storage devices to cause the storage devices to record the surgery data acquired by the acquiring devices and cause the storage devices to store the surgery data.

The surgery data according to the present embodiment includes, for example, image data, patient vital data, log data of medical devices used in surgery, and sound data which is collected by a sound input device such as a microphone. Image data included in the surgery data includes, for example, data representing images captured for medical purposes which is generated by performing imaging using the overhead camera 12, the surgical area camera 14, and the endoscope/medical apparatus 16 (examples of medical observation equipment) and the like. Furthermore, the image data included in the surgery data may also include sound. Patient vital data included in the surgery data includes, for example, data indicating the pulse of the patient, data indicating the blood pressure of the patient, and data indicating the blood loss of the patient. Log data of medical devices used in surgery includes, for example, data indicating settings when a treatment device (not illustrated) such as an electric scalpel or a bipolar device is functioning.

For example, by controlling the action of the switcher 46, the medical controller 10 causes the image data to be transmitted to the storage devices via the switcher 46. Furthermore, the medical controller 10 may access the storage devices and the patient information management devices and read surgery data and patient information which are stored in the storage devices and the patient information management devices, respectively.

The medical controller 10 also controls the action of the data output devices to cause the surgery data and/or patient information to be output from the data output devices. More specifically, the medical controller 10 causes the image data included in the currently acquired surgery data to be output from the data output devices according to a user instruction, for example. In addition, the medical controller 10 causes one, two, or more of the medical device log data, the vital data, the anesthesia data (described subsequently), the electronic medical record information (described subsequently) and the DICOM information (described subsequently), which are included in the currently acquired surgery data, to be output from the data output devices according to a user instruction, for example. Note that, in cases where a plurality of data output devices exist, as per the configuration example illustrated in FIG. 1, mutually different data may be output from each device according to a user instruction.

An illumination device 50 that projects illuminating light on the surgical area may also be connected to the medical controller 10. The illumination device 50 is a shadowless light, for example. The medical controller 10 may also control the action of the illumination device 50 according to a user instruction.

The medical controller 10 is configured from a processor such as a central processing unit (CPU) or a digital signal processor (DSP), or the like, for example. The foregoing function is realized as a result of the processor of the medical controller 10 executing computation processing according to a predetermined program.

[1-2] Operating Devices

An operating device is a device enabling the person using the operating device to perform an operation.

As mentioned earlier, various equipment constituting the medical information processing system 1000 such as the medical controller 10, for example, are operated by operating an operating device. For example, the operating device for operating the medical controller 10 transmits an operation signal representing various instructions to the medical controller 10 in response to an operation by the person operating the operating device. The medical controller 10, which receives the operating signal transmitted from the operating device, controls the action of various connected equipment according to the instructions represented by the operation signal.

In addition, as mentioned earlier, the operating device may generate text data in cases where text is input by an operation to the operating device.

Operating devices include, for example, any devices enabling an operation to be performed, such as the touch panel 44 illustrated in FIG. 1, a mouse, a keyboard, various switches such as a foot switch, or a lever or remote controller. Further, an operating device may be a sound collection device such as a microphone, or an imaging device such as a digital video camera. A sound collection device functions as an operating device for performing operations involving sound, and an imaging device functions as an operating device for performing operations involving movements or shapes such as gestures.

[1-3] Acquiring Devices

An acquiring device is a device that acquires various surgery data. Acquiring devices include, for example, as mentioned earlier, the overhead camera 12, the surgical area camera 14, the endoscope/medical apparatus 16, the external input terminal 18, the intercom 20, the biometric monitor 22, and the anesthesia system 24.

The overhead camera 12 is installed on the ceiling of the operating room and captures images of an aspect inside the operating room (in particular, an aspect in the periphery of the operating table where the patient is located). The overhead camera 12 acquires, as surgery data, image data containing the aspect inside the operating room.

The surgical area camera 14 is installed close to the operating table inside the operating room, and captures images of a surgical area aspect. The surgical area camera 14 acquires, as surgery data, image data containing the surgical area aspect.

The endoscope/medical apparatus 16 represents, conceptually as one apparatus, an endoscope and various equipment used when treating a patient. Medical devices include, for example, "pneumoperitoneum devices for creating a surgical space extending the peritoneal cavity" and "treatment devices that solidify, dissect, or seal tissue by using high-frequency current energy or ultrasonic vibration energy", and the like. Note that medical devices are not limited to the foregoing examples and may include various equipment that is generally used in surgery. Using an endoscope, image data captured by the endoscope is acquired as surgery data. Furthermore, using a medical device, log data (that is, medical device log data) of settings when the medical device is functioning (for example, a setting for an air supply amount in the case of a pneumoperitoneum device and a setting for output power in the case of a treatment device, and so forth) is acquired as surgery data.

The external input terminal 18 is a terminal for inputting various data such as image data and log data. By connecting a device to the external input terminal 18, various data such as image data from the device is input to the medical information processing system 1000. In FIG. 1, a sensor device 58 is illustrated as a device that is connected to the external input terminal 18.

Note that, although a biometric sensor device is illustrated as the sensor device 58 in FIG. 1, the sensor device illustrated in FIG. 1 is an example, and an optional sensor device such as an IoT (Internet of Things) device or a wearable device may be connected to the external input terminal 18. Furthermore, it goes without saying that the sensor device 58 is not limited to be connected to the external input terminal 18. The sensor device 58 may also function as an acquiring device.

The intercom 20 functions as a microphone and acquires, as surgery data, sound data representing voice uttered inside the operating room. The voice represented by the sound data includes, for example, oral instructions by an advising physician and conversations between medical staff.

The biometric monitor 22 acquires, as surgery data, patient vital data (for example, data representing the pulse and blood pressure of a patient, and the like) during surgery.

The anesthesia system 24 is a system that performs various control and management relating to anesthesia during surgery, such as control of the administration of anesthesia to patients and management of anesthetic doses administered to patients. The anesthesia system 24 acquires anesthesia data as surgery data. Anesthesia data includes, for example, log data obtained in processes for performing various control and management relating to anesthesia, and data such as settings for anesthetic doses administered to patients.

Note that, in the medical information processing system 1000, a display device such as the wall monitor 40 may have a touch panel function. If a display device constituting the medical information processing system 1000 has a touch panel function, the display device may function as an acquiring device.

When a case where the wall monitor 40 has a touch panel function is taken as an example, an advising physician gives some kind of instruction to a primary surgeon by operating the display screen of the wall monitor 40 displaying an image captured by an endoscope, or the like, for example. At such time, data representing the instruction from the advising physician that has been input via the wall monitor 40 may function as annotation data for the image data displayed on the display screen of the wall monitor 40. Accordingly, in a case where the display device has a touch panel function, data corresponding to an operation to the display screen of the display device, such as the annotation data, may be acquired as surgery data in the medical information processing system 1000.

The respective image data acquired by the overhead camera 12, the surgical area camera 14, and the endoscope/medical apparatus 16 is transmitted using a predetermined transmission system via a converter 52 and input to the switcher 46. Furthermore, the image data acquired by the external input terminal 18 is transmitted using a predetermined transmission system via the converter 52 and input to the switcher 46. In addition, sound data acquired by the intercom 20 is transmitted using a predetermined transmission system via the converter 52 and input to the switcher 46.

The switcher 46 transmits the input data to the moving image server 28 via the converter 52 by a predetermined transmission system. At such time, in a case where annotation data has been acquired, the annotation data is transmitted by the switcher 46 to the moving image server 28 in association with the corresponding image data. The moving image server 28 stores the data transmitted from the switcher 46.

Furthermore, medical device log data that has been acquired by the medical devices of the endoscope/medical apparatus 16 is stored in the device log data server 30 via the medical controller 10. In addition, display data for the medical device log data acquired by the medical devices is transmitted via the converter 52 to the switcher 46 by a predetermined transmission system.

Further, the vital data and anesthesia data acquired by the biometric monitor 22 and the anesthesia system 24 are stored in the anesthesiology server 32. In addition, the display data among the vital data and anesthesia data acquired by the biometric monitor 22 and the anesthesia system 24 is transmitted via the converter 52 to the switcher 46 by a predetermined transmission system. As mentioned earlier, the biometric monitor 22 and the anesthesia system 24 may be installed independently of the medical controller 10. Hence, the vital data and anesthesia data acquired by the biometric monitor 22 and the anesthesia system 24 may be stored directly in the anesthesiology server 32 without passing via the medical controller 10. Furthermore, the display data among the vital data and anesthesia data may be transmitted directly to the switcher 46.

Note that, when acquiring surgery data, the acquiring device may acquire, simultaneously and in association with the surgery data, the time the surgery data was acquired. The acquiring device generates, as metadata for the surgery data, time data indicating the time the surgery data was acquired, for example.

Note that the foregoing acquiring device is an example and that the medical information processing system 1000 may also include another medical device that functions as an acquiring device. To cite an example, in a case where a blood loss amount of a patient and a transfusion amount administered to a patient are measured using a certain medical device at predetermined time intervals, the medical device functions as an acquiring device. The data indicating the blood loss amount and the like measured by the certain medical device is stored in the anesthesiology server 32 as patient vital data, for example. In addition, the certain medical device may generate the time the blood loss amount and the like was measured as metadata for the vital data.

[1-4] Storage Devices

Storage devices are devices that store surgery data. Storage devices include, for example, the recorder 26, the moving image server 28, the device log data server 30, and the anesthesiology server 32, as mentioned earlier.

The moving image server 28 stores image data among the surgery data, for example. The moving image server 28 receives, via the switcher 46, image data that has been acquired by the overhead camera 12, the surgical area camera 14, the endoscope/medical apparatus 16, and the external input terminal 18, and stores the image data, for example. At such time, in a case where image data and annotation data are acquired by the acquiring device, the medical controller 10 causes the moving image server 28 to store the annotation data in association with the image data.

The device log data server 30 receives, via the medical controller 10, the medical device log data acquired by the endoscope/medical apparatus 16 among the surgery data, and stores the medical device log data, for example.

The anesthesiology server 32 stores the vital data and anesthesia data acquired by the biometric monitor 22 and anesthesia system 24, respectively, among the surgery data, for example.

The recorder 26 functions as a backup device for the moving image server 28, the device log data server 30, and the anesthesiology server 32, for example. The recorder 26 stores all or part of the surgery data stored in the moving image server 28, the device log data server 30, and the anesthesiology server 32. The type of surgery data stored by the recorder 26 may be suitably determined by the user of the medical information processing system 1000. By providing the recorder 26, recovery of the surgery data is straightforward even if an anomaly should, by any chance, occur in the moving image server 28, the device log data server 30, or the anesthesiology server 32. Thus, the reliability of the medical information processing system 1000 is improved by providing the recorder 26. Note that, although only one recorder 26 is illustrated in FIG. 1, the medical information processing system 1000 may have a plurality of recorders 26. Furthermore, when there are a plurality of recorders 26, the data stored in each recorder may be the same, or all or part thereof may be different.

The recorder 26, the moving image server 28, the device log data server 30, and the anesthesiology server 32 may each store, in association with surgery data, electronic medical record information of patients that correspond to the surgery data, among the electronic medical record information (described subsequently) which is stored in the electronic medical record server 34. To cite an example, a patient ID and the ID of the primary surgeon performing the surgery, and the like (an example of the data contained in the electronic medical record information) are stored in association with the surgery data. "The transmission of electronic medical record information from the electronic medical record server 34 to the recorder 26, the moving image server 28, the device log data server 30, and the anesthesiology server 32, respectively," is achieved through control by the medical controller 10, for example.

[1-5] Patient Information Management Devices

Patient information management devices are devices that manage patient information. Patient information management devices include, for example, the electronic medical record server 34 and the DICOM server 36, as mentioned earlier.

The electronic medical record server 34 stores electronic medical record information.

As mentioned earlier, all or part of the data constituting the patient information is included in the electronic medical record information. To cite an example, electronic medical record information includes identification data uniquely identifying a patient (an ID identifying a patient, for example), patient biometric data, data indicating the medical history of the patient, and data indicating the surgical history of the patient, for example. The data indicating the surgical history of the patient may include the primary surgeon responsible for the surgery and an ID specifying the nurse participating in the surgery, and the like. Note that the electronic medical record information may also include optional data that may typically be included in order to implement the electronic medical record.

The DICOM server 36 stores patient DICOM information. DICOM information is stored on the DICOM server 36 in association with patient ID.

DICOM information includes, for example, CT image data representing CT (Computed Tomographic) images of patients and MRI image data representing MRI (Magnetic Resonance Imaging) images of patients. The DICOM information may also include optional DICOM-conformance data.

[1-6] Switcher 46

The switcher 46 is a device that controls inputs of various data such as image data to the respective devices and controls outputs of the various data from the respective devices. In the medical information processing system 1000, various data such as image data is input to the respective devices via the switcher 46 and is output from the respective devices via the switcher 46. The action of the switcher 46 is controlled by a switcher control device 48. In addition, the action of the switcher control device 48 is controlled by the medical controller 10. In other words, the medical controller 10 is capable of controlling the action of the switcher 46 via the switcher control device 48.

More specifically, as mentioned earlier, the switcher 46 transmits the image data acquired by the acquiring devices to the moving image server 28 via the converter 52 by a predetermined transmission system, for example. Furthermore, the switcher 46 acquires the surgery data acquired by the acquiring devices via the converter 52 by a predetermined transmission system.

The switcher 46 may also function based on a control signal transmitted from the medical controller 10. To cite an example, the switcher 46 transmits the surgery data to the data output device via the converter 52 by a predetermined transmission system, based on the control signal transmitted from the medical controller 10. Furthermore, to cite another example, the switcher 46 acquires electronic medical record information and/or DICOM information stored in the patient information management device based on the control signal transmitted from the medical controller 10 and transmits display data of the acquired information to the data output device via the converter 52 by a predetermined transmission system.

Note that a plurality of transmission paths of different transmission formats may be provided in the medical information processing system 1000 as transmission paths for transmitting the image data and the like. By providing a plurality of transmission paths of different transmission formats, even if an anomaly should, by any chance, occur in one transmission path in the medical information processing system 1000, the image data and the like can be transmitted normally by the other transmission path. Transmission systems include, for example, transmission systems corresponding to DVI (Digital Visual Interface), transmission systems corresponding to SDI (Serial Digital Interface) (HD-SDI, for example), and transmission systems using IP (Internet Protocol). Note that, in a case where a plurality of transmission paths of different transmission formats are provided, an external input terminal 18, the switcher 46, and the converter 52, which correspond to the adopted transmission systems, are provided in the medical information processing system 1000. In such a case, the external input terminal 18, switcher 46, and converter 52 may be provided for each transmission system in the medical information processing system 1000.

[1-7] Data Output Devices

Data output devices are devices that output acquired surgery data and/or patient information. Data output devices include, for example, the ceiling-mounted monitor 38, the wall monitor 40, and the printer 42, as mentioned earlier.

The ceiling-mounted monitor 38 is a display device that is installed suspended from the ceiling in the operating room. The wall monitor 40 is a display device that is installed on the wall inside the operating room.

The ceiling-mounted monitor 38 and the wall monitor 40 display, on a display screen, image data included in the surgery data, for example. Note that the ceiling-mounted monitor 38 and the wall monitor 40 may have an audio output device such as a loudspeaker. In other words, the ceiling-mounted monitor 38 and the wall monitor 40 are capable of outputting sound represented by sound data which is included in the surgery data, together with a display of images represented by image data.

Furthermore, the ceiling-mounted monitor 38 and the wall monitor 40 may display, on the display screen, content represented by one, two, or more of medical device log data, vital data, and anesthesia data, which are included in the surgery data, for example. Examples of the display of the respective data included in the surgery data include a display in the form of a graph plotted along a time axis.

Furthermore, the ceiling-mounted monitor 38 and the wall monitor 40 may display, in an optional format such as a table or image, the content represented by the electronic medical record information and/or DICOM information, for example.

Examples of the ceiling-mounted monitor 38 and the wall monitor 40 include a liquid crystal display, an organic EL (Electro-Luminescence) display, or a CRT (Cathode Ray Tube) display.

The printer 42 prints the content represented by the surgery data and/or patient information onto paper or the like.

The medical information processing system 1000 has a configuration illustrated in FIG. 1, for example. Note that the configuration of the medical information processing system according to the present embodiment is not limited to or by the configuration illustrated in FIG. 1. For example, the medical information processing system 1000 may also include various medical care-related devices such as an arm device 200, described subsequently.

[2] Processing Pertaining to Information Processing Method According to the Present Embodiment Processing pertaining to the information processing method according to the present embodiment will be described next by taking, as an example, a case where the medical information processing apparatus 100 illustrated in FIG. 1 performs processing pertaining to the information processing method according to the present embodiment.

[2-1] Overview of Information Processing Method According to the Present Embodiment As described with reference to FIG. 1, various data such as surgery data is generated and stored by each device in the medical information processing system 1000.

Here, it is assumed that, as the number of data items and data volume of the data stored in the devices constituting the medical information processing system 1000 (also including any devices that can be accessed from the medical information processing system 1000, similarly hereinbelow) increase, effective usage of such data will become increasingly difficult. By way of an example, when a case where a health worker such as a physician makes secondary usage of surgery data is assumed, as the number of data items and data volume of data stored in the devices constituting the medical information processing system 1000 increase, it is highly likely that the health worker will have to carry out a huge amount of work.

Hence, the medical information processing apparatus 100 extracts "data corresponding to a predetermined feature which is data corresponding to a predetermined selection condition" from the data stored in the devices constituting the medical information processing system 1000. Features according to the present embodiment include events relating to performed surgery such as patient and surgical-site conditions, acts by medical staff, and functional states of medical devices. Hereinbelow, data which is stored in devices constituting the medical information processing system 1000 and targeted for processing by the medical information processing apparatus 100 is represented as "candidate data".

Candidate data according to the present embodiment includes, for example, surgery data such as "surgery data acquired by the acquiring devices" described with reference to FIG. 1 and "stored in storage devices". Note that the candidate data is not limited to surgery data. For example, the candidate data may also include data other than surgery data, such as image data representing medical illustration images such as images illustrating autopsy diagrams.

Hereinbelow, data corresponding to the aforementioned predetermined selection conditions is represented as "target data". Furthermore, hereinbelow, "data, among the target data, which corresponds to a predetermined feature", that is, "data, among the candidate data, which corresponds to a predetermined selection condition and corresponds to a predetermined feature" is represented as "feature data". An example of target data and an example of feature data will be described subsequently.

As a result of the medical information processing apparatus 100 extracting feature data from the candidate data, the number of data items and data volume of the feature data is smaller than the number of data items and data volume of the data stored in the devices constituting the medical information processing system 1000. Thus, as a result of the medical information processing apparatus 100 extracting the feature data by processing pertaining to the information processing method according to the present embodiment, effective usage of the data stored in the devices constituting the medical information processing system 1000 is more straightforward.

Therefore, the medical information processing apparatus 100 enables improvements in health worker convenience.

[2-2] Example of Processing Pertaining to Information Processing Method According to the Present Embodiment Processing pertaining to the information processing method according to the present embodiment will be described in more specific terms hereinbelow.

The medical information processing apparatus 100 performs the selection processing indicated in (1) below and the extraction processing indicated in (2) below, for example, as processing pertaining to the information processing method according to the present embodiment.

(1) Selection Processing

The medical information processing apparatus 100 selects target data corresponding to a selection condition from the candidate data.

Selection conditions according to the present embodiment are conditions that include at least conditions relating to patient attributes, conditions relating to surgical-procedure types, and conditions relating to disease types.

Conditions relating to patient attributes include the examples listed below, for example.

Condition relating to patient gender: Male or female

Condition relating to patient age ranges (or ages): between 10 and 19 years, between 20 and 29 years, and so forth.

Condition relating to patient biometrics: One, two, or more of height, weight, and BMI (Body Mass Index), and so forth Combinations of the foregoing conditions Note that examples of conditions relating to patient attributes are not limited to or by the foregoing examples. For example, conditions relating to patient attributes may also include a condition to disregard patient gender. If a condition to disregard patient gender is set as a condition relating to patient attributes, target data that does not depend on patient attributes is then selected from among the candidate data.

Conditions relating to surgical-procedure types include, for example, the name of a procedure or an ID uniquely identifying the procedure, or the like, and optional conditions enabling a surgical procedure to be specified.

Note that examples of conditions relating to surgical-procedure types are not limited to or by the foregoing examples. For example, conditions relating to surgical-procedure types may also include a condition to disregard a surgical-procedure type. If a condition to disregard a surgical-procedure type is set as a condition relating to surgical-procedure types, target data that does not depend on the surgical-procedure type is then selected from among the candidate data.

Conditions relating to disease types include, for example, the name of a disease or an ID uniquely identifying the disease, or the like, and optional conditions enabling a disease to be specified.

Note that examples of conditions relating to disease types are not limited to or by the foregoing examples. For example, conditions relating to disease types may also include a condition to disregard a disease type. If a condition to disregard a disease type is set as a condition relating to disease types, target data that does not depend on the disease type is then selected from among the candidate data.

Selection conditions according to the present embodiment include "conditions that include the foregoing conditions relating to patient attributes, conditions relating to surgical-procedure types, and conditions relating to disease types".

Note that the selection conditions according to the present embodiment are not limited to or by the foregoing examples. For example, the selection conditions may also include one, two, or more of conditions relating to the primary surgeon and conditions relating to administered medication, and the like. Conditions relating to the primary surgeon include, for example, the name of the primary surgeon or an ID uniquely identifying the primary surgeon, or the like, and optional conditions enabling the primary surgeon to be specified. Conditions relating to medication include, for example, the name of the medication or an ID uniquely identifying the medication, or the like, and optional conditions enabling the medication to be specified.

The selection conditions are set by an operation to an operating unit (described subsequently) which the medical information processing apparatus 100 comprises or by an operation to an operating device external to the medical information processing apparatus 100 such as a remote controller, for example.

Note that the selection condition setting method is not limited to an operation-based setting method. For example, the medical information processing apparatus 100 is also capable of setting a selection condition based on surgery data acquired during surgery.

Examples of setting a selection condition based on surgery data include setting a selection condition based on the results of analyzing sound represented by sound data and setting a selection condition based on the results of analyzing images captured for medical purposes, for example. In a case where predetermined sound is recognized as a result of optional sound recognition processing of sound, the medical information processing apparatus 100 sets a selection condition which corresponds to the recognized sound, for example. Furthermore, in a case where a predetermined movement by a health worker, or a predetermined medical device or medical instrument is recognized as a result of optional image recognition processing of images captured for medical purposes, the medical information processing apparatus 100 sets a selection condition which corresponds to the recognition results, for example.

Automatic setting of selection conditions is achieved as a result of selection conditions being set based on surgery data, as mentioned above, for example. Moreover, "in a case where a procedure is modified during surgery, target data corresponding to the modified procedure is automatically selected, and feature data corresponding to the modified procedure is automatically extracted" is achieved as a result of selection conditions being set automatically, for example.

The medical information processing apparatus 100 selects target data by directly accessing the storage device constituting the medical information processing system 1000 and searching for the data satisfying the selection condition from among the data stored by the storage device (an example of data including the candidate data, similarly hereinbelow), for example. The selection of target data according to the present embodiment signifies "specifying the location where the target data is stored" or "acquiring the retrieved target data from the location where the target data is stored", for example.

In addition, the medical information processing apparatus 100 may cause an external device to search for the data satisfying the selection condition by transmitting "a control signal containing an instruction to search for data satisfying the selection condition and an instruction to issue a response indicating a search result" to an external device such as the medical controller 10, for example. In this case, the external device selects the target data by searching for data satisfying the selection condition from among the data stored by the storage device.

The medical information processing apparatus 100 or the external device receiving the control signal searches for data satisfying the selection condition by performing processing pertaining to an optional information search technique on the data stored by the storage device, such as candidate data which is surgery data and the like, and metadata associated with the candidate data, for example.

(2) Extraction Processing

When target data is selected by the selection processing, the medical information processing apparatus 100 searches for a feature from among the selected target data and extracts, from the target data, feature data corresponding to the detected feature.

A feature according to the present embodiment is detected based on the functional state of a specified medical device (for example, a treatment device such as an electric scalpel or a bipolar device), a patient condition, movements of a health worker in the operating room, the content of utterances made by the health worker in the operating room, or a combination of the foregoing, for example.

For example, the medical information processing apparatus 100 detects, as a feature, a point in time when a treatment device switches from a non-functional state to a functional state or a point in time when a treatment device switches from a functional state to a non-functional state. The medical information processing apparatus 100 detects a feature based on medical device log data (an example of surgery data).

In addition, the medical information processing apparatus 100 detects, as a feature, a point in time when patient vitals fluctuate greatly, for example. The medical information processing apparatus 100 detects a feature by threshold value processing using patient vital data (an example of surgery data), for example.

Furthermore, the medical information processing apparatus 100 detects, as a feature, a point in time when a predetermined action by a health worker is detected in the operating room, for example. The medical information processing apparatus 100 detects a feature by performing optional image recognition processing on an image captured for medical purposes which is represented by image data (an example of surgery data) representing an image captured for medical purposes, for example. Image data representing an image captured for medical purposes sometimes appears as "medical captured image" hereinbelow.

In addition, the medical information processing apparatus 100 detects, as a feature, a point in time when text is input in a case where predetermined wording is detected from among text that is input by an operation to an operating device, for example. The medical information processing apparatus 100 detects a feature by performing optional syntactic analysis processing, or the like, on text which is represented by text data (an example of surgery data), for example.

Furthermore, the medical information processing apparatus 100 detects, as a feature, a point in time when predetermined utterance content by a health worker is detected in the operating room, for example. The medical information processing apparatus 100 detects a feature by performing optional sound recognition processing on sound represented by sound data (an example of surgery data), for example.

In other words, the medical information processing apparatus 100 detects a state-related feature and/or an action-related feature from target data. State-related features include, for example, the aforementioned feature based on the functional state of a specified medical device and the aforementioned feature based on a patient condition. Action-related features include, for example, the aforementioned feature based on movement of a health worker in the operating room and the aforementioned feature based on the content of utterances made by a health worker in the operating room.

As per the foregoing examples, the medical information processing apparatus 100 detects, as a state-related feature, "a point in time in target data when a predetermined state is detected from target data". Furthermore, the medical information processing apparatus 100 detects, as an action-related feature, "a point in time in target data when a predetermined action is detected from target data". In other words, the features according to the present embodiment may also be regarded as specified points in time relating to states or specified points in time relating to actions. In addition, the feature data according to the present embodiment can be regarded as data corresponding to a point in time when a predetermined state is assumed or data corresponding to a point in time when a predetermined action is performed.

Upon detecting a feature, the medical information processing apparatus 100 extracts feature data corresponding to a detected feature from target data, as mentioned earlier.

Here, feature data corresponding to a detected feature includes target data in which a feature is detected.

For example, in a case where a feature has been detected from a medical captured image, the medical information processing apparatus 100 extracts, as feature data, a medical captured image (still image) captured at a point in time when a feature is detected or medical captured images (moving image) captured in a set period which includes a point in time when a feature is detected. Furthermore, in a case where a feature has been detected from sound data, for example, the medical information processing apparatus 100 extracts, as feature data, sound data collected at a point in time when a feature is detected or sound data collected in a set period which includes a point in time when a feature is detected. In addition, in a case where a feature has been detected from text data, for example, the medical information processing apparatus 100 extracts the text data as feature data.

Note that feature data corresponding to detected features is not limited to or by the foregoing examples. For example, feature data corresponding to detected features may be optional target data associated with target data in which a feature is detected.

To cite an example, in a case where target data in which a feature is detected is a medical captured image, the medical information processing apparatus 100 extracts, as feature data, a medical illustration image which corresponds to a medical captured image captured at a point in time when the feature is detected. Medical illustration images which correspond to a medical captured image include, for example, autopsy diagrams with a matching (or similar) procedure or case, and the like. In a case where target data in which a feature is detected is a medical captured image, the medical information processing apparatus 100 is also capable of extracting, as feature data, text data that represents text which has been input by an operation to an operating device in a set period which includes a point in time when the feature is detected.

Furthermore, to cite another example, in a case where target data in which a feature is detected is sound data, the medical information processing apparatus 100 extracts, as feature data, a medical captured image captured at a point in time when the feature is detected or text data that is input in a set period which includes a point in time when the feature is detected. To cite yet another example, in a case where the target data in which a feature is detected is text data, the medical information processing apparatus 100 extracts, as feature data, a medical captured image captured at a point in time when the text data was input or sound data collected in a set period which includes a point in time when the text data was input.

It goes without saying that examples of target data associated with target data in which a feature is detected are not limited to or by the foregoing examples. Furthermore, the medical information processing apparatus 100 is also capable of extracting, as feature data, target data in which a feature is detected, and target data associated with target data in which one, two, or more features are detected.

The medical information processing apparatus 100 may extract, as feature data, at least data of a specified type that has been set, for example.

For example, medical images according to the present embodiment for which the medical information processing apparatus 100 extracts, as feature data, at least image data representing medical images include optional images relating to medical care such as medical captured images and/or medical illustration images, for example. Image data representing medical images sometimes appears as "medical images" hereinbelow.

Generally, images recognized visually by a health worker have a larger information volume than media recognized by the other senses of the health worker such as sound. Accordingly, by extracting at least medical images as feature data, the medical information processing apparatus 100 is capable of extracting feature data with a larger information volume. Furthermore, extracting feature data with a larger information volume is advantageous in editing processing, described subsequently, and display control processing, described subsequently, for example.

The medical information processing apparatus 100 extracts the feature data by machine learning, for example. More specifically, the medical information processing apparatus 100 extracts feature data by using a model learned through machine learning, for example. Machine learning includes learning pertaining to the detection of features from target data and/or learning pertaining to the extraction of feature data from target data, for example. Machine learning according to the present embodiment includes, for example, machine learning by an optional learning method such as deep learning or deep reinforcement learning, which is a combination of deep learning and reinforcement learning. To cite specific examples, learning includes, for example, learning in which the medical information processing apparatus 100 uses a recurrent neural network and learning in which the medical information processing apparatus 100 uses a Long Short-Term Memory neural network.

As per the earlier examples, the medical information processing apparatus 100 detects a feature from selected target data and extracts feature data corresponding to the detected feature from the target data, for example. The medical information processing apparatus 100 extracts feature data whenever target data is selected in the processing (selection processing) of (1) above, in other words, whenever a selection condition changes.

Note that the extraction processing according to the present embodiment is not limited to or by the foregoing example.

For example, the medical information processing apparatus 100 may issue a notification regarding the grounds for extracting the feature data. The medical information processing apparatus 100 issues a notification regarding rule-based extraction grounds or knowledge-based extraction grounds, for example. The medical information processing apparatus 100 issues a notification regarding the grounds for extracting the feature data, namely, "a visual notification by displaying, on the display screen of a display device, an image indicating the grounds and/or a character string indicating the grounds", "an auditory notification by outputting, from a sound output device, sound indicating the grounds", or a combination of such notifications.

As a result of the medical information processing apparatus 100 issuing a notification regarding the grounds for extracting the feature data, a health worker is able to recognize the grounds for extracting the feature data. Thus, as a result of the medical information processing apparatus 100 issuing a notification regarding the grounds for extracting the feature data, feature data which is extracted by processing pertaining to the information processing method according to the present embodiment is then data which is easy for a health worker to accept.

The medical information processing apparatus 100 performs the processing (selection processing) of (1) above and the processing (extraction processing) of (2) above, for example, as processing pertaining to the information processing method according to the present embodiment.

Here, feature data is extracted from candidate data as a result of performing the processing (selection processing) of (1) above and the processing (extraction processing) of (2) above. Furthermore, the number of data items and data volume of the feature data is smaller than the number of data items and data volume of the candidate data, that is, the data stored in the devices constituting the medical information processing system 1000. Thus, as a result of the feature data being extracted, the effective usage of the data stored in the devices constituting the medical information processing system 1000 is more straightforward.

Therefore, by performing the processing (selection processing) of (1) above and the processing (extraction processing) of (2) above, for example, the medical information processing apparatus 100 enables improvements in health worker convenience.

Note that the processing pertaining to the information processing method according to the present embodiment is not limited to or by the processing (selection processing) of (1) above or the processing (extraction processing) of (2) above. For example, the medical information processing apparatus 100 is also capable of performing processing using extracted feature data.

Figure 2:
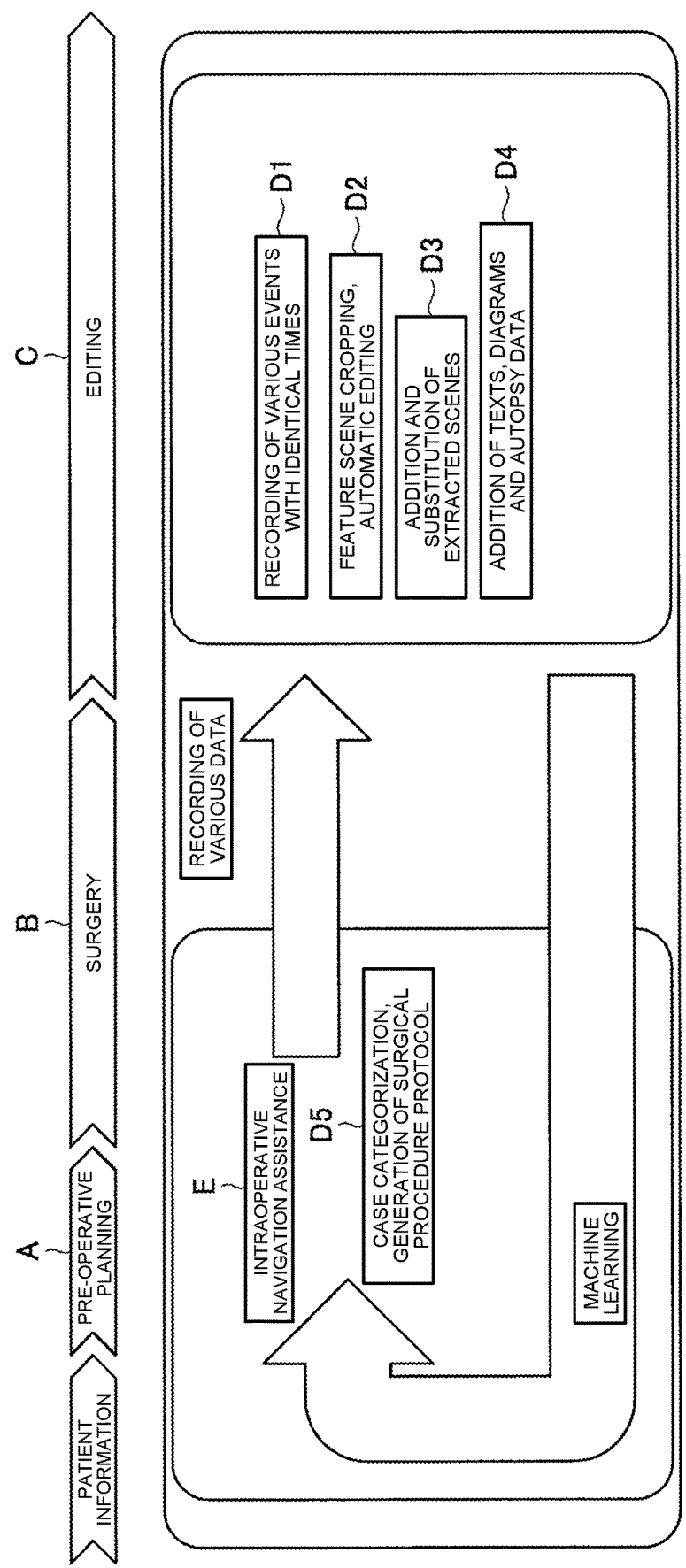
FIG. 2 is an explanatory drawing serving to illustrate processing pertaining to an information processing method according to the present embodiment.

FIG. 2 is an explanatory drawing serving to illustrate processing pertaining to the information processing method according to the present embodiment. The pre-operative planning process illustrated in A of FIG. 2, the surgical process illustrated in B of FIG. 2, and the editing process illustrated in C of FIG. 2 represent an example of a process flow in a case where surgery is performed on a certain patient.

Assuming use cases that utilize extracted feature data, the use cases that may be considered are use cases where feature data is utilized after performing surgery on a certain patient and/or use cases where feature data is utilized while surgery is being performed on a certain patient.

Processing corresponding to use cases where feature data is utilized after performing surgery on a certain patient includes "editing processing using extracted feature data", for example. An example of editing processing is the processing indicated in D1 to D5 illustrated in FIG. 2.

One such example of processing corresponding to a use case where feature data is utilized while surgery is being performed on a certain patient is "display control processing that causes a display screen to display medical images (an example of feature data) that correspond to surgery data acquired during surgery", for example. By performing display control processing, health worker assistance such as the intraoperative navigation assistance (navigation assistance during surgery) indicated in E illustrated in FIG. 2, for example, is realized.

Furthermore, another example of processing corresponding to a use case where feature data is utilized while surgery is being performed on a certain patient is "arm control processing that controls the action of an arm based on feature data that corresponds to surgery data acquired during surgery", for example.

An arm according to the present embodiment is an arm capable of carrying a medical instrument, for example. The arm according to the present embodiment is configured by interconnecting a plurality of links by joint sections, for example. The degrees of freedom of the arm according to the present embodiment can be set to afford the arm the desired degrees of freedom according to the number and placement of joint sections and links and the directions of the drive shafts of the joint sections, and the like, for example. An example of the arm according to the present embodiment will be described subsequently.

Here, the arm according to the present embodiment may be an arm which a device external to the medical information processing apparatus 100 comprises or may be an arm which the medical information processing apparatus 100 comprises. An example of a case where the arm according to the present embodiment is an arm of a device external to the medical information processing apparatus 100 will be the main focus hereinbelow.

In other words, the medical information processing apparatus 100 may perform all or part of the editing processing, the display control processing, and the arm control processing as processing which uses extracted feature data pertaining to the information processing method according to the present embodiment.

Note that processing which uses extracted feature data pertaining to the information processing method according to the present embodiment is not limited to the editing processing, the display control processing, or the arm control processing. For example, the medical information processing apparatus 100 is also capable of performing optional processing which uses extracted feature data such as "processing in which a storage device constituting the medical information processing system 1000 is made to store extracted feature data" or "processing in which the extracted feature data is transmitted to a device external to the medical information processing system 1000".

As an example of processing which uses extracted feature data pertaining to the information processing method according to the present embodiment, editing processing, display control processing, and arm control processing will each be described hereinbelow.

(3) Editing Processing

The medical information processing apparatus 100 edits extracted feature data. The medical information processing apparatus 100 edits the feature data based on an operation by the user of the medical information processing apparatus 100 or automatically. Examples of editing processing include the processing indicated in D1 to D5, respectively, which is illustrated in FIG. 2, as mentioned earlier.

Figure 3:
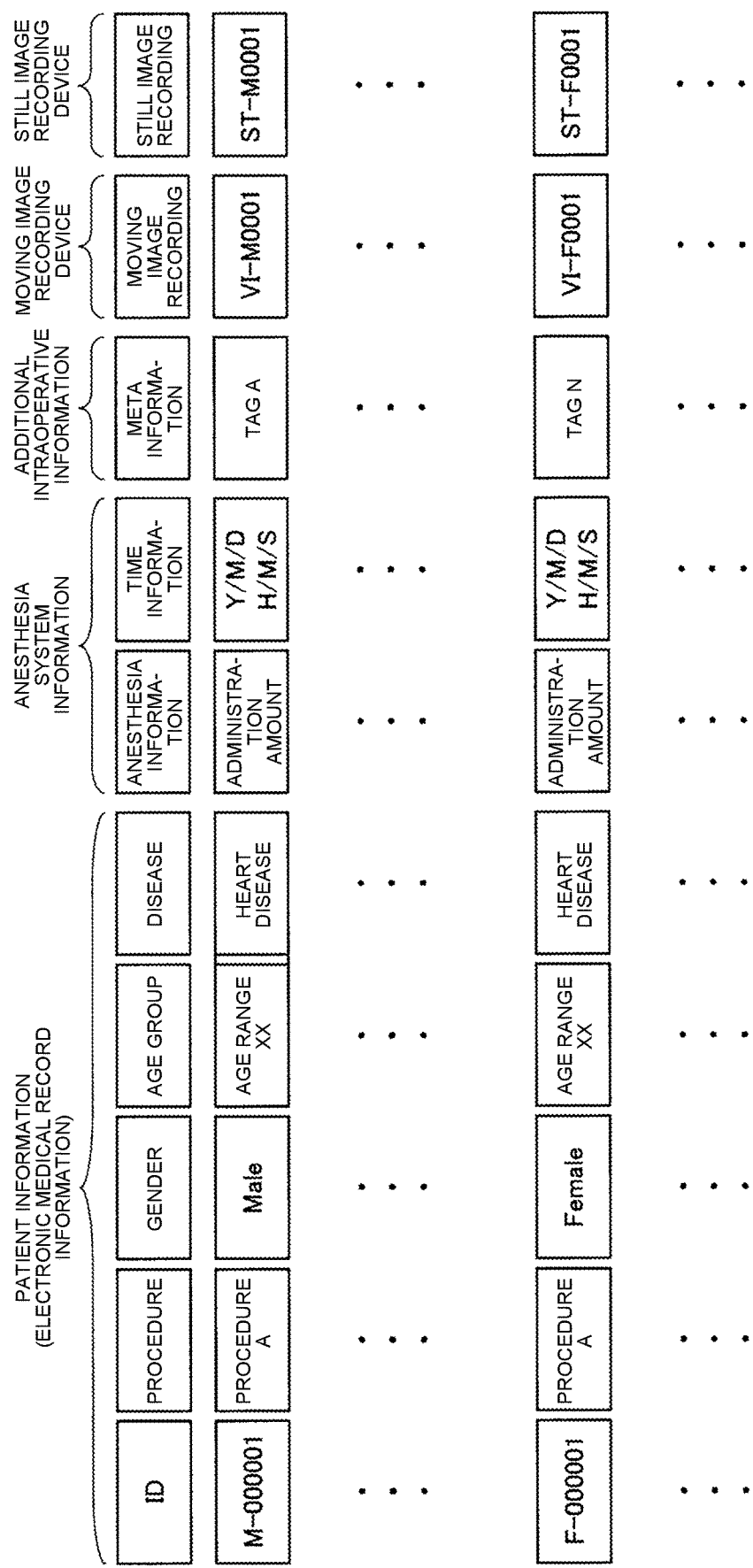
FIG. 3 is an explanatory drawing serving to illustrate an example of editing processing pertaining to the information processing method according to the present embodiment.
Figure 4:
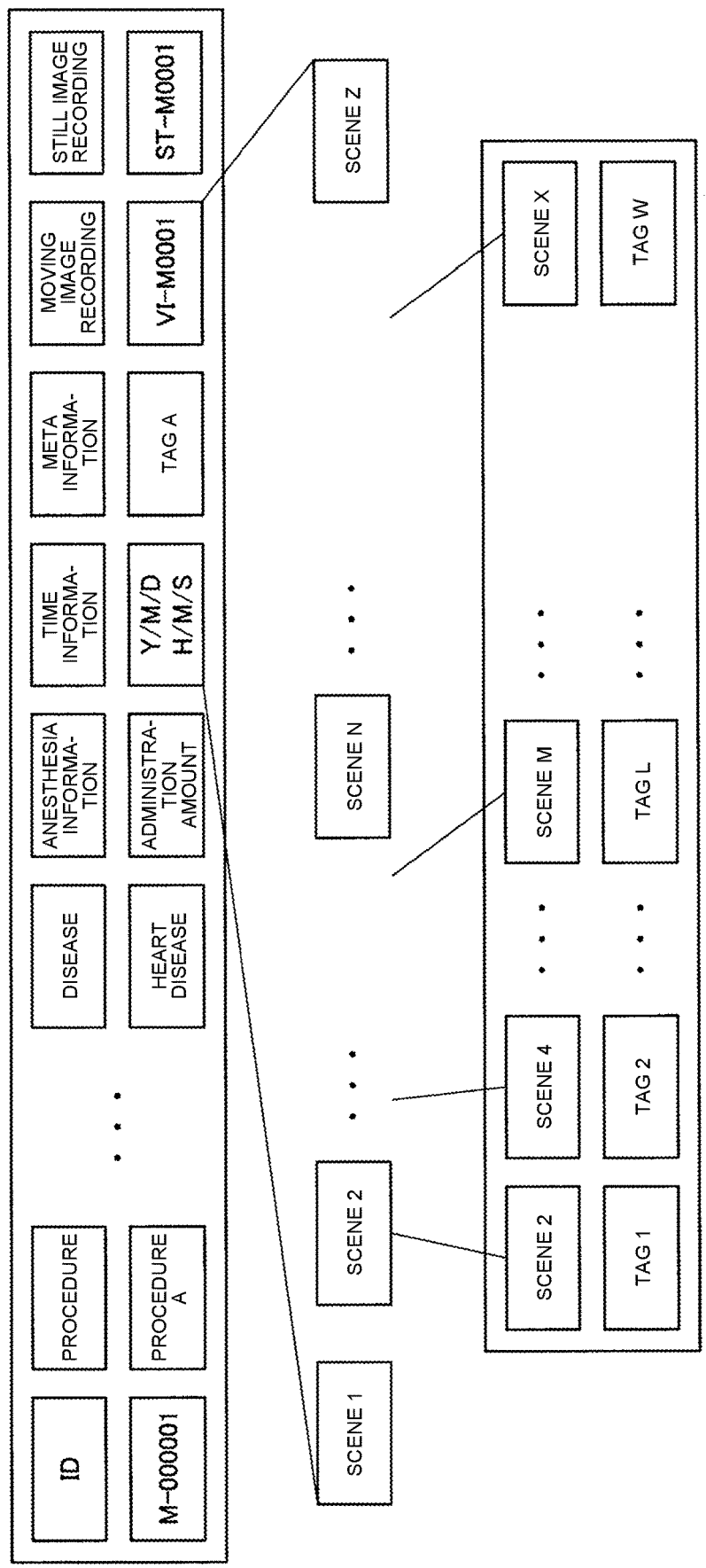
FIG. 4 is an explanatory drawing serving to illustrate an example of editing processing pertaining to the information processing method according to the present embodiment.
Figure 5:
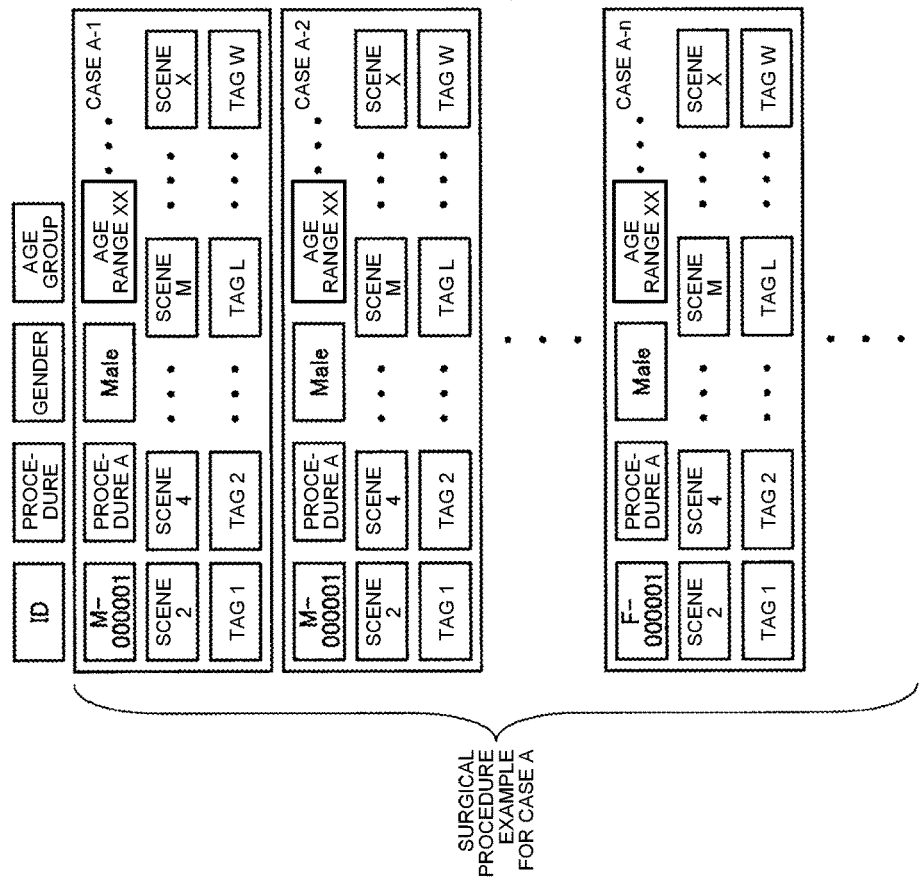
FIG. 5 is an explanatory drawing serving to illustrate an example of editing processing pertaining to the information processing method according to the present embodiment.

FIGS. 3 to 5 are explanatory drawings serving to illustrate an example of editing processing pertaining to the information processing method according to the present embodiment. FIG. 3 illustrates an example of candidate data which is stored in devices constituting the medical information processing system 1000. FIG. 4 is an explanatory diagram that conceptually illustrates an example of the results of editing processing, and FIG. 5 is an explanatory diagram that conceptually illustrates another example of the results of editing processing.

The processing pertaining to the automatic editing indicated in D2 of FIG. 2 is given as an example. As illustrated in FIG. 4, for example, whenever a case is implemented, the medical information processing apparatus 100 generates, as one case file and together with tag data (metadata), a main surgery scene which is extracted by the processing (extraction processing) indicated in (2) above.

Processing pertaining to the generation of the surgical procedure protocol indicated in D5 of FIG. 2 is given as an example. As illustrated in FIG. 5, for example, the medical information processing apparatus 100 creates a protocol file (protocol data) representing a protocol for a case A from a plurality of case files corresponding to case A. The protocol for case A corresponds to a surgical procedure manual for case A. In addition, the protocol file created by the medical information processing apparatus 100 corresponds to a surgical procedure manual that represents the best practices for case A.

The medical information processing apparatus 100 creates the protocol file for case A from a plurality of case files based on an operation or the like with respect to an operating unit (described subsequently) which the medical information processing apparatus 100 comprises (an example of manual editing).

Furthermore, in a case where a group of patients with the same attributes has been selected by an operation or the like with respect to the operating unit (described subsequently), the medical information processing apparatus 100 may automatically create the protocol file for case A, for example (an example of automatic editing). Patient attributes include, for example, optional metrics which are included in patient information (or combinations of optional metrics included in patient information) such as age range, weight, and BMI, and the like.

The medical information processing apparatus 100 automatically creates a protocol file for case A by "calculating an average distribution from patient attributes (average age, average weight, BMI, and the like) and automatically selecting image examples, and the like, which are suitable for case A from among a group of patient attributes including the average values", and so forth, for example. In addition, the medical information processing apparatus 100 may use machine learning to automatically select image examples, and the like, which are suitable for case A from among extracted feature data.

For example, as a result of the medical information processing apparatus 100 creating a case protocol file for a selected group of patients with the same attributes, "the automatic creation of a protocol for each case and each patient attribute" is realized by the medical information processing system 1000.

For example, after the protocol file for case A has been created as described above, the medical information processing apparatus 100 is also capable of manual or automatic substitution of image examples, and the like, which are suitable for case A by machine learning and/or by an operation or the like with respect to an operating unit (described subsequently). In other words, the created case protocol file may be suitably updated by editing processing.

The medical information processing apparatus 100 edits extracted feature data as above, for example. It goes without saying that examples of editing processing are not limited to or by the example above.

(4) Display Control Processing

The medical information processing apparatus 100 causes a display screen to display medical images (an example of feature data) corresponding to surgery data acquired during surgery. By displaying medical images corresponding to surgery data on a display screen, health worker assistance such as the intraoperative navigation assistance indicated in E illustrated in FIG. 2, for example, is realized, as mentioned earlier. In other words, medical images corresponding to surgery data may correspond to navigation images during surgery.

Display screens for displaying the medical images include optional display devices such as the ceiling-mounted monitor 38 and the wall monitor 40 which are illustrated in FIG. 1, for example. The medical information processing apparatus 100 causes the display screen to display the medical images corresponding to the surgery data by transmitting, to the display device, a control signal containing a display instruction and image data representing the medical images corresponding to the surgery data, for example.

The medical information processing apparatus 100 causes the medical images to be displayed on the whole display screen, for example. The medical information processing apparatus 100 may also cause the medical images to be displayed in a partial area of the display screen by a PIP (Picture In Picture) display or a POP (Picture Out Picture) display, or the like, for example.

Figure 6:
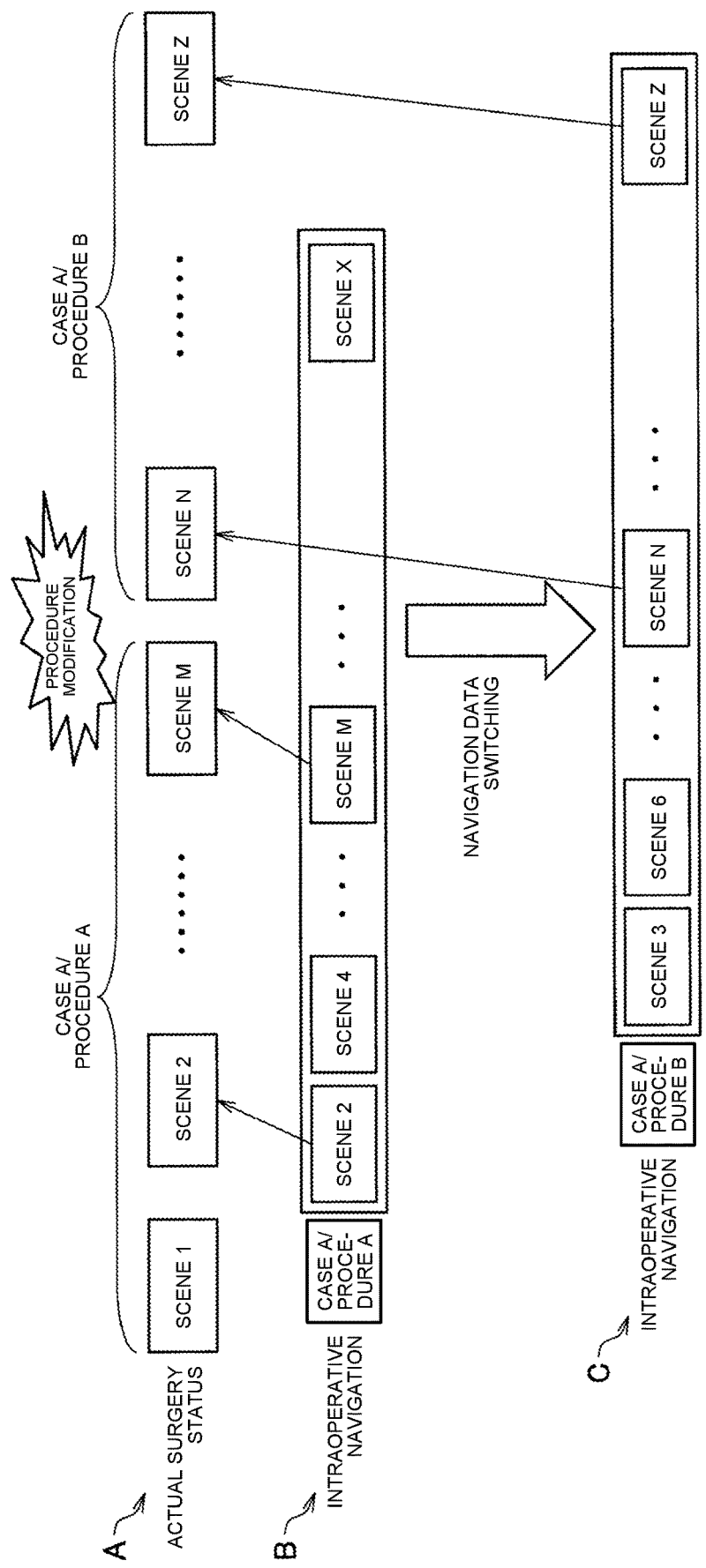
FIG. 6 is an explanatory drawing serving to illustrate an example of display control processing pertaining to the information processing method according to the present embodiment.

FIG. 6 is an explanatory drawing serving to illustrate an example of display control processing pertaining to the information processing method according to the present embodiment.

A of FIG. 6 illustrates surgery statuses which are specified from surgery data acquired during surgery. In A of FIG. 6, surgery statuses are illustrated by being divided up into individual scenes in which a feature is detected. Features corresponding to surgery statuses are detected as per the feature detection in the processing (extraction processing) indicated in (2) above.

B of FIG. 6 conceptually illustrates medical images for each scene which are displayed on the display screen as part of intraoperative navigation assistance that corresponds to a case A and a procedure A. C of FIG. 6 conceptually illustrates medical images for each scene which are displayed on the display screen as part of intraoperative navigation assistance that corresponds to a case A and a procedure B.

When intraoperative navigation assistance is being performed, the medical information processing apparatus 100 causes the display screen to display the medical image corresponding to the next scene ahead of the actual surgery status, as indicated in A of FIG. 6 and B of FIG. 6.

In a medical setting, the procedure is sometimes modified during surgery, according to the situation. If the procedure is modified according to the situation, the medical information processing apparatus 100 causes the display screen to display "a medical image which corresponds to the modified procedure and corresponds to the next scene" ahead of the actual surgery status, as indicated in A of FIG. 6 and C of FIG. 6.

The medical information processing apparatus 100 causes the display screen to display "a medical image which corresponds to the modified procedure and corresponds to the next scene" based on an operation to an operating unit (described subsequently) or the like which the medical information processing apparatus 100 comprises, for example.

The medical information processing apparatus 100 may also cause the display screen to display "a medical image which corresponds to the modified procedure and corresponds to the next scene" based on the results of detecting a procedure modification which is detected from surgery data, for example. The medical information processing apparatus 100 detects a procedure modification from surgery data as a result of optional image recognition processing of medical captured images, as a result of optional sound recognition processing of sound, or a combination thereof, for example.

In a case where "a medical image which corresponds to the modified procedure and corresponds to the next scene" is displayed on the display screen, the medical information processing apparatus 100 may also "issue a notification regarding "the grounds for extracting the medical images displayed on the display screen". The "grounds for extracting the medical images displayed on the display screen" are equivalent to the aforementioned "grounds for extracting the feature data", which correspond to the medical images displayed on the display screen.

As a result of the medical information processing apparatus 100 issuing a notification regarding the "grounds for extracting the medical images displayed on the display screen", an advantageous effect is afforded whereby "intraoperative navigation assistance by the medical images displayed on the display screen is then easy for a health worker to accept".

Note that, in a medical setting, a plurality of procedures are sometimes carried out in a single surgery performed on a patient as a result of pre-operative planning. Even when a plurality of procedures are carried out, the medical information processing apparatus 100 is capable of performing intraoperative navigation assistance in switching procedures, similarly to the aforementioned case where a procedure is modified according to the situation, during the surgery.

The medical information processing apparatus 100 causes a display screen to display medical images corresponding to surgery data acquired during surgery, as mentioned earlier, for example.

Note that examples of display control processing are not limited to or by the foregoing example. For example, the medical information processing apparatus 100 may also notify a health worker of the content of feature data that corresponds to the medical images displayed on the display screen. To cite an example, the medical information processing apparatus 100 outputs sound corresponding to the medical images from a sound output device in conjunction with intraoperative navigation assistance using a display of medical images.

(5) Arm Control Processing

The medical information processing apparatus 100 controls the action of an arm capable of carrying a medical instrument.

(5-1) Example of an Arm Device and Example of the Action of the Arm Device 200.

Before describing arm control processing, an example of an arm device comprising an arm capable of carrying a medical instrument according to the present embodiment and an example of the action of the arm device 200 will be described.

Figure 7:
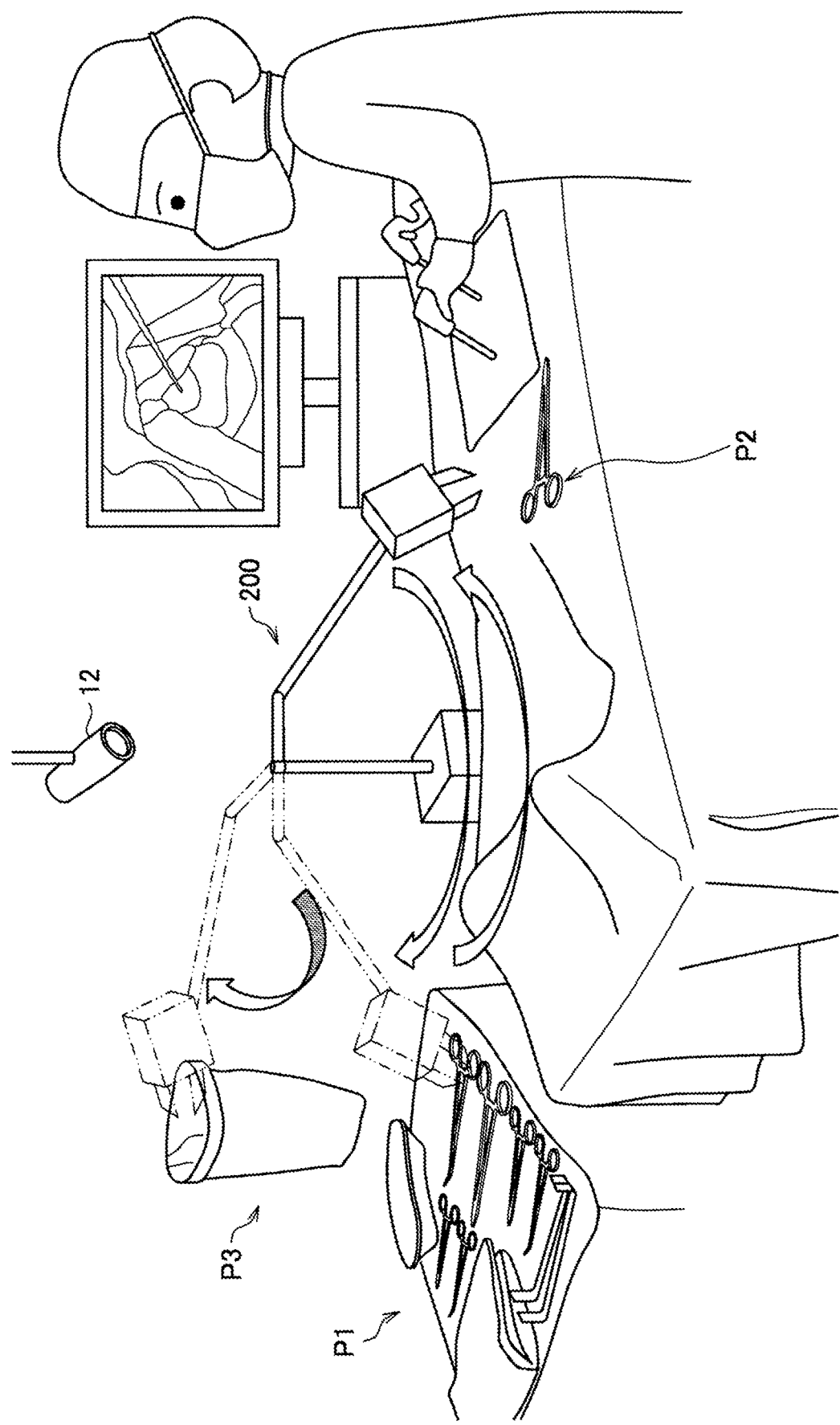
FIG. 7 is an explanatory drawing serving to illustrate an example of arm control processing pertaining to the information processing method according to the present embodiment.

FIG. 7 is an explanatory drawing serving to illustrate an example of arm control processing pertaining to the information processing method according to the present embodiment. FIG. 7 illustrates an example of a surgical setting in which the arm device 200 comprising an arm capable of carrying a medical instrument is used.

In a surgical setting, the handing over of medical devices used by a primary surgeon is performed by a scrub nurse. Meanwhile, in the medical field, the problem of a scrub nurse shortage has been recognized. Hence, going forward, it may be assumed that devices such as the arm device 200 illustrated in FIG. 7 will assume the role of scrub nurses.

As mentioned earlier, the arm device 200 is a device that comprises an arm which is configured by interconnecting a plurality of links by joint sections, and that carries a medical instrument through movement of the arm, for example. FIG. 7 illustrates "an example in which the arm device 200 moves between an equipment storage location P1, an equipment installation location P2, and an equipment disposal location P3, carrying medical instruments between each of the locations"

Note that the locations to which the arm device 200 carries medical instruments are not limited to or by the examples illustrated in FIG. 7. For example, the arm device 200 is capable of carrying a medical instrument to a variety of locations such as "a location storing medical instruments undergoing a sterilization treatment among the medical instruments used during surgery". In addition, in a case where a medical instrument is carried to a "location storing medical instruments undergoing a sterilization treatment among the medical instruments used during surgery", for example, the equipment disposal location P3 need not be provided. "An example in which the arm device 200 moves between an equipment storage location P1, an equipment installation location P2, and an equipment disposal location P3 and carries a medical instrument between each of the locations" will be described hereinbelow.

The equipment storage location P1 is a storage location where medical instruments which are scheduled to be used in surgery are placed and corresponds to a so-called Mayo stand. The equipment installation location P2 is a storage location where medical instruments, which are used by the primary surgeon and carried from the equipment storage location P1, are placed. The equipment disposal location P3 is a storage location where medical instruments for disposal among used medical instruments are gathered. Note that the storage locations storing medical instruments are not limited to the equipment storage location P1, the equipment installation location P2, and the equipment disposal location P3. For example, the storage locations according to the present embodiment may also include an additional equipment storage location where medical instruments added during surgery are placed.

Figure 8:
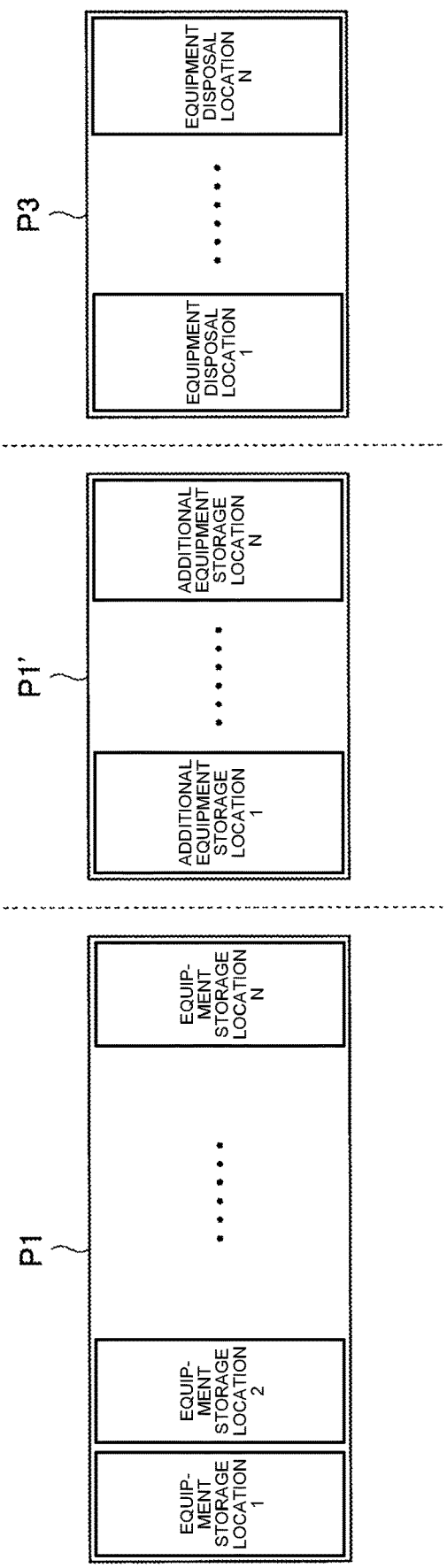
FIG. 8 is an explanatory drawing serving to illustrate an example of a medical instrument storage location according to the present embodiment.

FIG. 8 is an explanatory drawing serving to illustrate an example of a medical instrument storage location according to the present embodiment. FIG. 8 illustrates, as storage locations, the equipment storage location P1, an additional equipment storage location P1', and the equipment disposal location P3. Note that, although the equipment storage location P1 and additional equipment storage location P1' are separate in FIG. 8, the equipment storage location P1 and additional equipment storage location P1' may also be the same storage location (the same Mayo stand, for example).

Medical instruments are placed beforehand in the equipment storage location P1 prior to the start of surgery. In the equipment storage location P1, the locations where medical instruments are placed are uniquely categorized, as illustrated in FIG. 8, for example. Note that, in a case where the medical instruments placed in the equipment storage location P1 can be uniquely specified by captured images captured by the overhead camera 12, or by sensors, or the like, the locations where the medical instruments are placed in the equipment storage location P1 need not be categorized. A medical instrument may be specified by recognizing a shape or pattern, or the like, from a captured image or by reading an RFID (Radio Frequency IDentification) from an RF (Radio Frequency) tag given to the medical instrument, for example.

The association of medical instruments with locations in the equipment storage location P1 is performed when the medical instruments are placed in the equipment storage location P1, for example, and information indicating an association result is stored in a storage unit (described subsequently) which the medical information processing apparatus 100 comprises. Note that the association of medical instruments with locations in the equipment storage location P1 may also be performed automatically by the medical information processing apparatus 100 or performed manually by an operation using an operating unit (described subsequently) which the medical information processing apparatus 100 comprises. Information indicating an association result includes, for example, data that associates an ID representing the location where a medical instrument is placed with a medical instrument ID, data representing the shape of a medical instrument, and data representing the RFID of the RF tag given to a medical instrument, and the like. Information indicating an association result may also include disposal information indicating whether a medical instrument has been disposed of after use (a flag or the like indicating whether or not the medical instrument has been disposed of, for example). Disposal information is set automatically or manually.

Medical instruments added during surgery are placed in the additional equipment storage location P1'. In a case where a medical instrument is placed in the additional equipment storage location P1', association of the medical instrument with a location in the additional equipment storage location P1' is performed in the same way as placement of medical instruments in the equipment storage location P1.

Medical instruments which are disposed of, such as gauze and needles, are gathered in the equipment disposal location P3. As illustrated in FIG. 8, locations where the medical instruments are disposed of in the equipment disposal location P3 are uniquely categorized, and items for disposal are separated. Note that, in cases where there is no need to separate items for disposal, there may be one location for disposing of medical instruments in the equipment disposal location P3.

Figure 9:
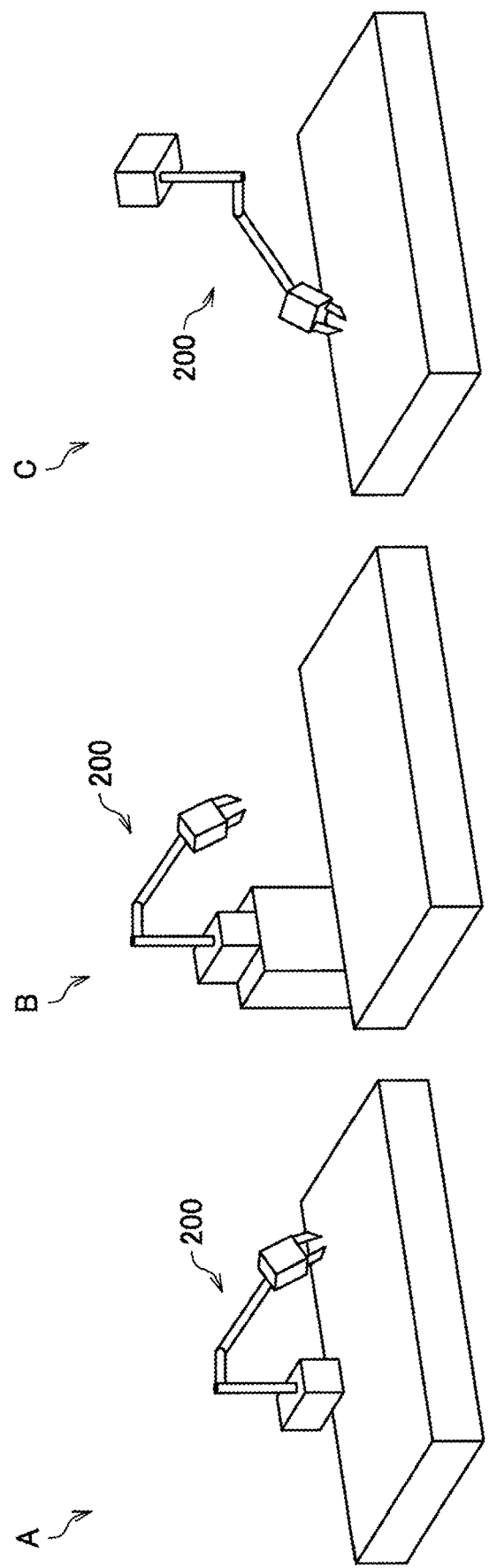
FIG. 9 is an explanatory drawing illustrating an example of the structure of an arm device according to the present embodiment.

FIG. 9 is an explanatory drawing illustrating an example of the structure of the arm device 200 according to the present embodiment. The arm device 200 may have a structure that mounts on the bed rail of a surgery bed as illustrated in A of FIG. 9, a structure that integrates with a pedestal as illustrated in B of FIG. 9, or a ceiling pendant structure that hangs from the ceiling as illustrated in C of FIG. 9, for example. Note that the structure of the arm device 200 is not limited to the examples illustrated in FIG. 9 and may have any structure enabling a medical instrument to be carried by causing an arm to move.

The arm device 200 comprises a processor (not illustrated) that controls the action of the whole arm device 200; a communication device (not illustrated) that enables wired or wireless communication with an external device such as the medical information processing apparatus 100; a casing; an arm; and a retaining member provided at the end of the arm, for example. The arm device 200 is driven by electrical power supplied from an internal power source such as a battery which the arm device 200 comprises or electrical power supplied from a connected external power source, or the like, for example.

Processors (not illustrated) include, for example, a micro processing unit (MPU) or a CPU, or the like. Furthermore, communication devices (not illustrated) include, for example, a communication antenna and an RF circuit (wireless communication), an IEEE 802.15.1 port and a transceiver circuit (wireless communication), an IEEE 802.11 port and a transceiver circuit (wireless communication), or a LAN terminal and a transceiver circuit (wired communication), or the like. The processor (not illustrated) and communication device (not illustrated) are provided in the casing, for example.

The retaining member is provided at the end of the arm and retains medical instruments of various sizes and shapes.

Figure 10:
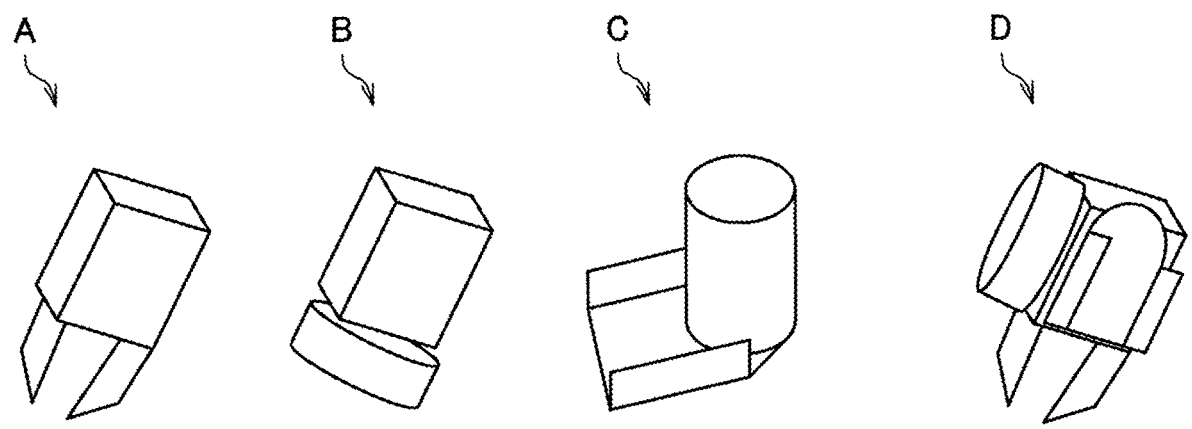
FIG. 10 is an explanatory drawing illustrating an example of a retaining member provided at an end of an arm of the arm device according to the present embodiment.

FIG. 10 is an explanatory drawing illustrating an example of a retaining member provided at the end of the arm of the arm device 200 according to the present embodiment. The retaining member retains various medical instruments as a result of having a structure (A of FIG. 10) that grips a medical instrument, a structure that attracts a medical instrument by a magnetic force or air (B of FIG. 10), a scoop-type structure that scoops up a medical instrument (C of FIG. 10), or a structure combining the foregoing structures (D of FIG. 10), for example. Note that the structure of the retaining member is not limited to the examples illustrated in FIG. 10 and the arm device 200 may have an optional structure capable of retaining one, two, or more medical instruments.

In addition, the retaining member is configured from a material enabling sterilization treatment and has a mechanism enabling attachment to/detachment from the arm. Mechanisms enabling the retaining member to be removed from the arm include, for example, optional mechanisms enabling the retaining member to be removed from the arm such as a latch attachment/detachment mechanism, a button attachment/detachment mechanism, or a thumb-turn attachment/detachment mechanism. Because the retaining member is configured from a material enabling sterilization treatment and having a mechanism enabling attachment to/detachment from the arm, the arm device 200 is compatible with actions in sanitary areas of a surgical setting.

Note that the retaining member need not be configured from a material enabling sterilization treatment. In this case, the retaining member is made disposable, and the arm device 200 can be made compatible with actions in sanitary areas of a surgical setting through the suitable disposal of the retaining member.

The retaining member includes an optional sensor which is capable of detecting stress that is applied at the time of an action such as when someone grasps a medical instrument, for example, and releases a medical instrument by weakening the gripping force when a specified stress is detected.

The retaining member is supplied with electrical power from the arm device 200 itself, wirelessly or via a cable, for example. In addition, the retaining member and a processor (not illustrated) are connected to each other wirelessly or via a cable, for example, and perform signal transmission and reception by communicating wirelessly or via a cable.

The arm device 200 comprises a casing, a processor (not illustrated), a communication device (not illustrated), an arm, and the retaining member, for example.

Note that the configuration of the arm device 200 is not limited to or by the foregoing example. For example, the arm device 200 may further comprise a distance sensor (not illustrated) which is capable of measuring the distance to an object using an optional system such as a time-of-flight (TOF) system, for example.

One, two, or more distance sensors (not illustrated) are provided on a part which is not touched by a health worker during normal use, such as on part of the arm of the arm device 200, and the sensor(s) measure(s) the distance to an object in the vicinity of the part. One, two, or more distance sensors (not illustrated) are arranged so as to measure the distance to objects that exist all around the foregoing part which is not touched by a health worker during normal use, for example. Note that the sensing range of the one, two, or more distance sensors (not illustrated) may be optionally set at the design stage or manufacturing stage, or the like, for example.

The distance sensor (not illustrated) is connected to the processor (not illustrated) wirelessly or via a cable, for example, and transmits a signal representing a detection result by wireless communication or wired communication. The processor (not illustrated), which receives the detection result, controls the action of the arm based on the distance indicated by the signal representing the detection result. To cite an example, when the distance indicated by the signal representing the detection result is equal to or less than a set threshold value (or if the distance is less than the threshold value), the processor (not illustrated) reduces the speed of the moving arm, stops the arm, or changes the trajectory of the retaining member (the travel route of the retaining member) provided at the end of the arm.

For example, by controlling the action of the arm based on the detection result from the distance sensor (not illustrated) as above, the arm device 200 is able to predict collisions with people and obstacles and the like and safely reduce the speed of the arm, safely stop the arm, or safely avoid a collision of the arm.

It goes without saying that the sensor for implementing arm movement to safely reduce the speed of the arm, stop the arm, or avoid a collision of the arm is not limited to a distance sensor (not illustrated).

Moreover, even in a case where the arm device 200 does not comprise a distance sensor (not illustrated) or the like, the processor (not illustrated) of the arm device 200 is capable of implementing arm movement to safely reduce the speed of the arm, stop the arm, or avoid a collision of the arm by performing image processing on captured images captured by the overhead camera 12, for example. The processor (not illustrated) recognizes a "relative positional relationship between the arm device 200, people, and obstacles, and the like, based on captured images," and performs control of the arm according to the recognition result, for example.

Figure 11:
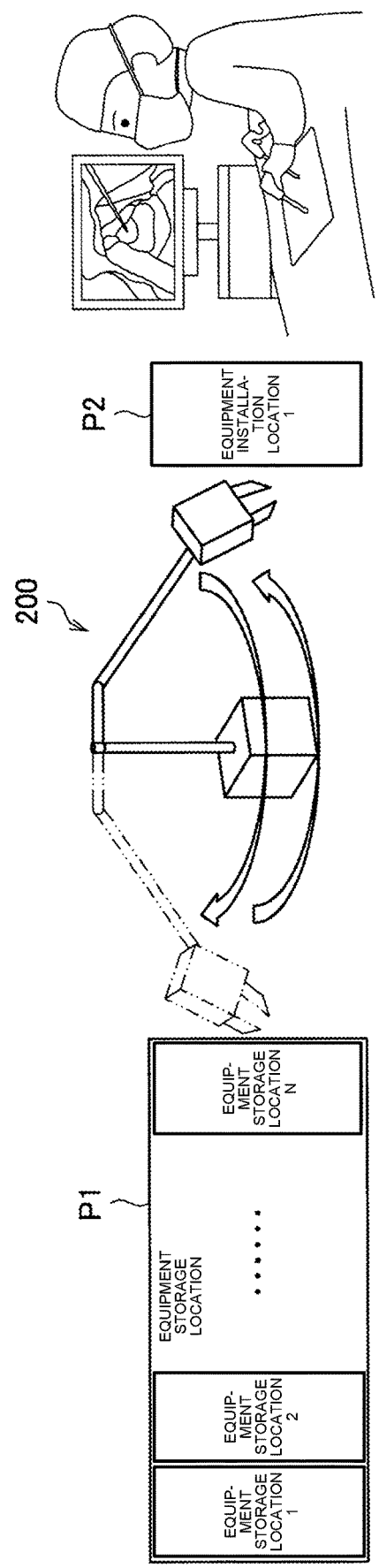
FIG. 11 is an explanatory drawing illustrating an example of the action of the arm device according to the present embodiment.
Figure 12:
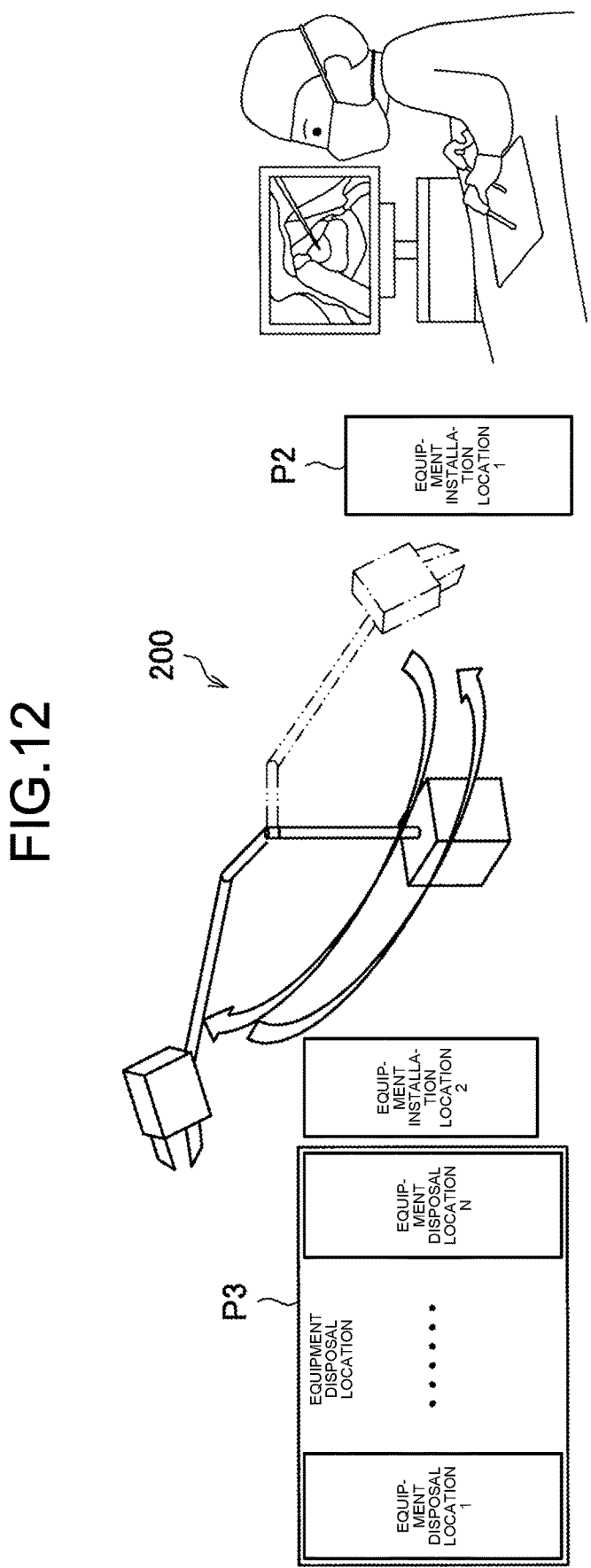
FIG. 12 is an explanatory drawing illustrating an example of the action of the arm device according to the present embodiment.

FIGS. 11 and 12 are explanatory drawings illustrating an example of the action of the arm device 200 according to the present embodiment. FIG. 11 illustrates an example of an action in which a medical instrument is carried from the equipment storage location P1 to the equipment installation location P2. Furthermore, FIG. 12 illustrates an example of an action in which a medical instrument is carried from the equipment installation location P2 to the equipment disposal location P3.

First, an example of a case where a medical instrument is carried from the equipment storage location P1 to the equipment installation location P2 will be described.

The arm device 200 carries a specified medical instrument among the medical instruments stored in the equipment storage location P1 to the equipment installation location P2 according to a control signal corresponding to arm control processing by the medical information processing apparatus 100, for example.

Note that the arm device 200 is also capable of carrying a specified medical instrument among the medical instruments stored in the equipment storage location P1 to the equipment installation location P2 based on an operation by a health worker. Operations pertaining to the carrying of a medical instrument include, for example, an operation to an operating device such as a remote controller, a voice-based operation to a sound input device such as a microphone, an operation based on a line of sight detected by an optional imaging device, and an operation based on movement detected by an optional imaging device, and the like.

Various operations are recognized by the medical information processing apparatus 100, for example. The medical information processing apparatus 100 transmits a control signal corresponding to a recognized operation to the arm device 200. Furthermore, the arm device 200 carries a specified medical instrument among the medical instruments stored in the equipment storage location P1 to the equipment installation location P2 according to a control signal corresponding to the operation.

Upon carrying the medical instrument from the equipment storage location P1 to the equipment installation location P2, the arm device 200 moves the retained medical instrument to the equipment installation location P2. The arm device 200 then moves the arm to a predetermined standby position. Furthermore, the arm device 200 carries the medical instrument from the equipment storage location P1 to the equipment installation location P2 and may move the arm to the predetermined standby position if stress, which is applied during an action such as when a primary surgeon or someone else grasps the medical instrument, is detected.

Predetermined standby positions include, for example, an initial set position and a position (a spatial position with no person or obstacle, for example) which is set based on a captured image captured by the overhead camera 12. The processing pertaining to setting the predetermined standby position may be performed by the processor (not illustrated) of the arm device 200 or may be performed by the medical information processing apparatus 100.

Next, an example of a case where a medical instrument is carried from the equipment installation location P2 to the equipment disposal location P3 will be described.

Similarly to a case where a medical instrument is carried from the equipment storage location P1 to the equipment installation location P2, the arm device 200 carries a medical instrument stored in the equipment installation location P2 to the equipment disposal location P3 in accordance with a control signal corresponding to the arm control processing by the medical information processing apparatus 100, for example. Furthermore, similarly to a case where a medical instrument is carried from the equipment storage location P1 to the equipment installation location P2, the arm device 200 may carry a medical instrument stored in the equipment installation location P2 to the equipment disposal location P3 based on an operation by a health worker.

The arm device 200 retains a medical instrument stored in the equipment installation location P2 by gripping, or the like, of the medical instrument, and carries the retained medical instrument to the equipment disposal location P3. In addition, the arm device 200 is also capable of retaining the medical instrument by gripping, or the like, of the medical instrument, which is handed over by a health worker such as the primary surgeon, and is capable of carrying the retained medical instrument to the equipment disposal location P3, for example.

Similarly to a case where a medical instrument is carried from the equipment storage location P1 to the equipment installation location P2, upon carrying a medical instrument from the equipment installation location P2 to the equipment disposal location P3, for example, the arm device 200 places the retained medical instrument in the equipment disposal location P3 and moves the arm to a predetermined standby position. Furthermore, similarly to a case where a medical instrument is carried from the equipment storage location P1 to the equipment installation location P2, the arm device 200 may move the arm to the predetermined standby position if stress, which is applied during an action such as when a primary surgeon or someone else grasps the medical instrument, is detected, for example.

(5-2) Example of Arm Control Processing

An example of arm control processing for realizing the foregoing action of the arm device 200 will be described next.

As mentioned earlier, the medical information processing apparatus 100 causes the arm device 200 to function by transmitting a control signal that controls the action of the arm of the arm device 200 to the arm device 200.

To cite an example, the medical information processing apparatus 100 specifies a surgery progress status based on feature data corresponding to surgery data acquired during surgery. Further, the medical information processing apparatus 100 controls the action of the arm of the arm device 200 so that the medical instrument corresponding to the specified progress status is carried to a predetermined position that corresponds to the progress status.

As per the feature detection in the processing (extraction processing) indicated in (2) above, the medical information processing apparatus 100 detects a feature corresponding to the surgery status and specifies the surgery progress status from the detected feature. The act of specifying the surgery progress status corresponds to the specifying of the scene in which the feature is detected as illustrated in A of FIG. 6, for example.

Upon specifying the surgery progress status, the medical information processing apparatus 100 specifies the medical instrument and the storage location of the medical instrument which correspond to the specified surgery progress status. The medical information processing apparatus 100 specifies the specified medical instrument corresponding to the surgery progress status and the specified medical instrument storage location corresponding to the surgery progress status (the location to which the medical instrument will be carried) by referring to "a table (or database) that associates information indicating surgery progress statuses and medical instruments being used with information indicating storage locations" which is stored on a recording medium such as a storage unit (described subsequently), for example.

Information indicating a medical instrument includes, for example, data of an optional format enabling a medical instrument to be specified such as data representing the ID of the medical instrument, data representing the shape of the medical instrument, and data representing the RFID of the RF tag given to the medical instrument. Information indicating a medical instrument includes, for example, data configured by an operation by the user or the like of the medical information processing apparatus 100 and/or data configured as a result of the medical information processing apparatus 100 performing machine learning.

Information indicating storage locations includes, for example, data indirectly indicating a storage location such as data representing the ID corresponding to the equipment storage location P1, data representing the ID corresponding to the equipment installation location P2, data representing the ID corresponding to the equipment disposal location P3, and data representing the ID corresponding to the additional equipment storage location P1'. Furthermore, information indicating storage locations may be information that directly indicates a storage location such as data representing the spatial coordinates of each storage location.

The medical information processing apparatus 100 then transmits, to the arm device 200, a control signal that includes "a control instruction for carrying the specified medical instrument corresponding to the surgery progress status to the specified storage location corresponding to the surgery progress status".

For example, as mentioned earlier, the medical information processing apparatus 100 is capable of controlling the action of the arm device 200 in conjunction with intraoperative navigation assistance by transmitting a control signal corresponding to the surgery progress status specified based on feature data to the arm device 200. Furthermore, by controlling the action of the arm device 200 in conjunction with intraoperative navigation assistance, the medical information processing apparatus 100 implements "the arm device 200 automatically carries the medical instrument corresponding to the surgery progress status to the storage location corresponding to the surgery progress status even in the absence of an operation by a health worker such as a primary surgeon"

Figure 13:
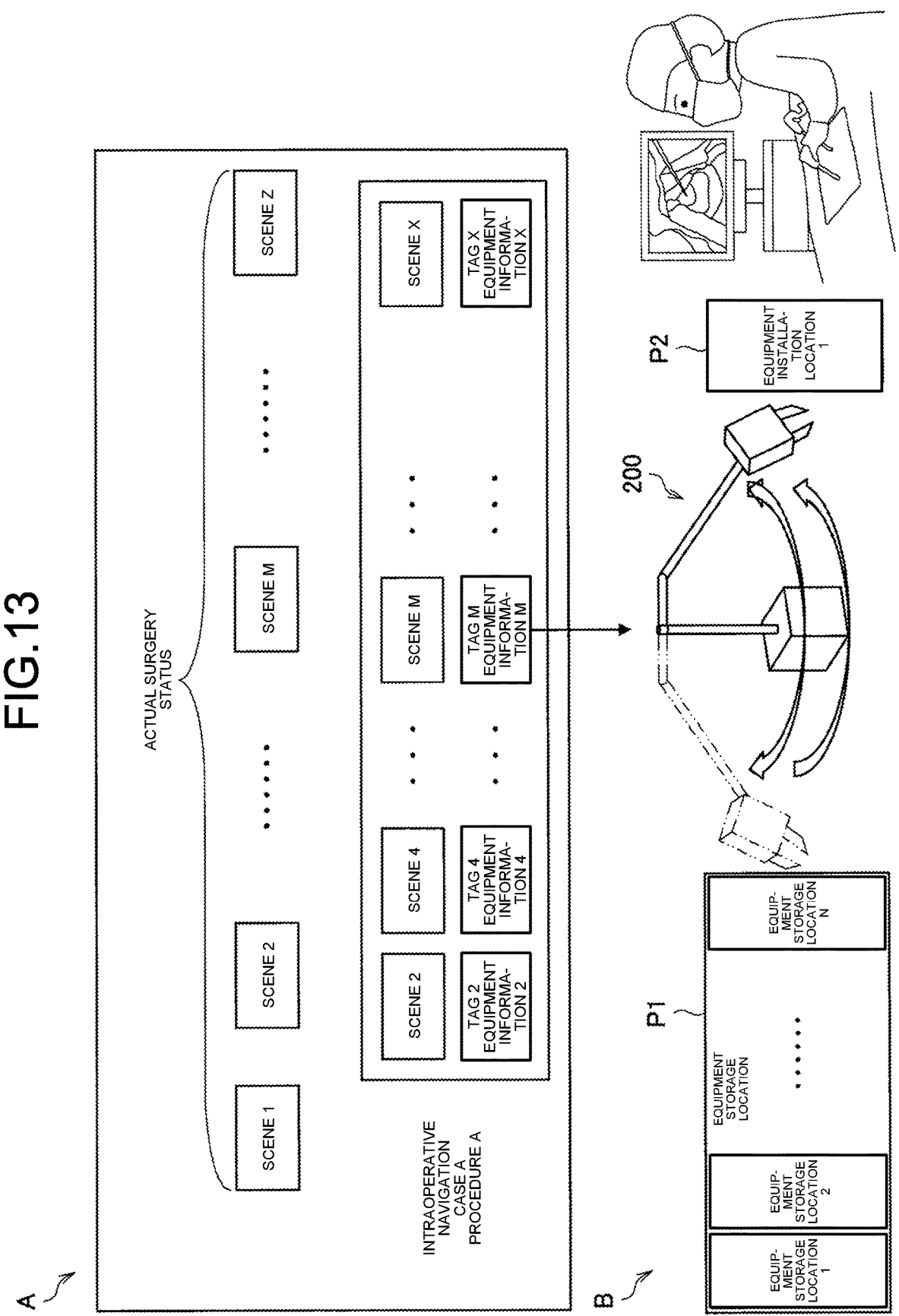
FIG. 13 is an explanatory drawing serving to illustrate an example of arm control processing pertaining to the information processing method according to the present embodiment.

FIG. 13 is an explanatory drawing serving to illustrate an example of arm control processing pertaining to the information processing method according to the present embodiment. Similarly to FIG. 6, A of FIG. 13 indicates an example of the relationship between the actual surgery status and intraoperative navigation. B of FIG. 13 illustrates an example of control of the action of the arm device 200 in conjunction with intraoperative navigation assistance.

For example, as illustrated in FIG. 13, the medical information processing apparatus 100 specifies a scene which corresponds to the actual surgery status and carries the medical instrument corresponding to the specified scene to the equipment installation location P2 which is the storage location corresponding to the specified scene.

Note that the arm control processing according to the present embodiment is not limited to or by the foregoing example. For example, the medical information processing apparatus 100 is also capable of recognizing various operations such as an operation to an operating device or a voice-based operation and of transmitting a control signal corresponding to a recognized operation to the arm device 200. As a result of the medical information processing apparatus 100 transmitting a control signal corresponding to the recognized operation to the arm device 200, a health worker such as a primary surgeon is able to cause the arm device 200 to perform an intended action.

(Medical Information Processing Apparatus According to the Present Embodiment)

An example of a configuration of the medical information processing apparatus 100 which enables the processing pertaining to the information processing method according to the present embodiment to be performed will be described next.

[I] Example of Configuration of Medical Information Processing Apparatus 100

Figure 14:
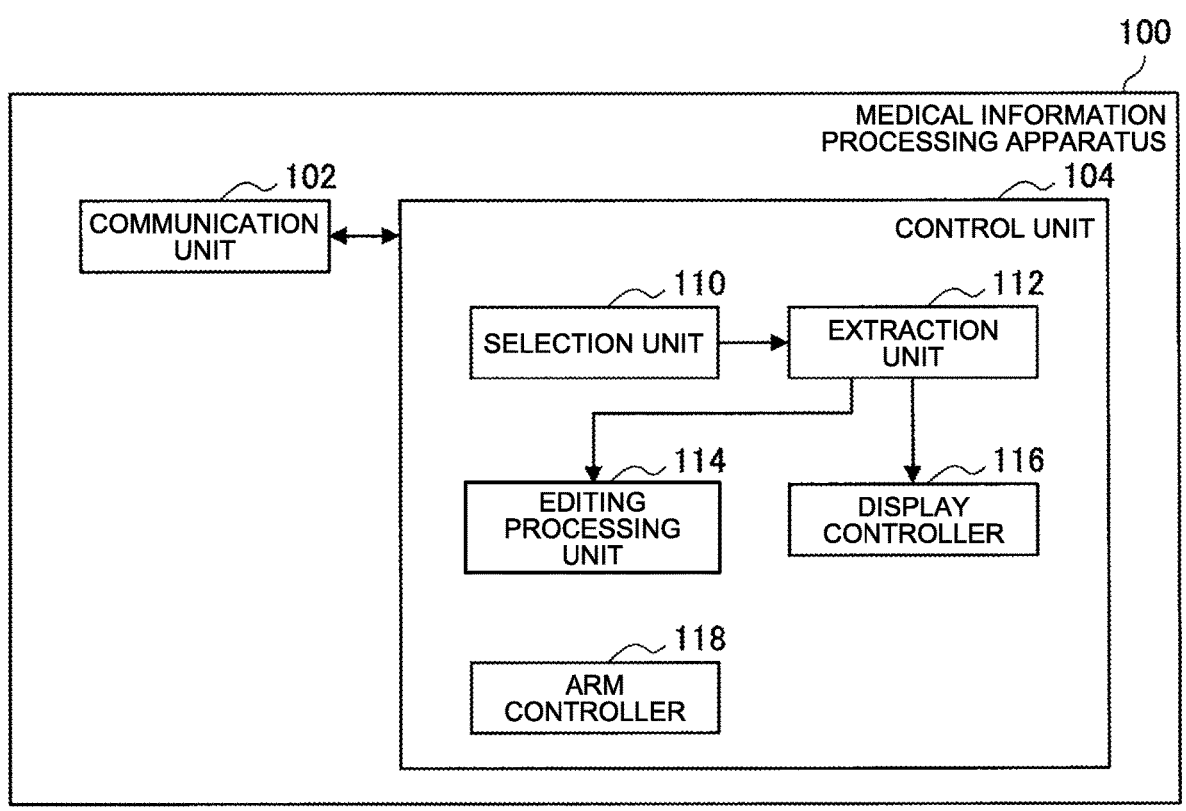
FIG. 14 is a block diagram illustrating an example of the configuration of the medical information processing apparatus according to the present embodiment.

FIG. 14 is a block diagram illustrating an example of the configuration of the medical information processing apparatus 100 according to the present embodiment. The medical information processing apparatus 100 comprises a communication unit 102 and a control unit 104, for example.

Furthermore, the medical information processing apparatus 100 may also comprise, for example, a read-only memory (ROM; not illustrated), a random-access memory (RAM; not illustrated), a storage unit (not illustrated), an operating unit (not illustrated) which a user of the medical information processing apparatus 100 is able to operate, and a display unit (not illustrated) that displays various screens on a display screen, and the like. The medical information processing apparatus 100 interconnects various components by a bus which constitutes a data transmission path, for example.

The ROM (not illustrated) stores control data such as programs, calculation parameters, and the like, which are used by the control unit 104. The RAM (not illustrated) temporarily stores programs executed by the control unit 104, and the like.

The storage unit (not illustrated) is a storage means which the medical information processing apparatus 100 comprises and stores various data such as, for example, various applications, and data pertaining to the information processing method according to the present embodiment such as "machine learning-related data, including information indicating a network structure, hyperparameters and training data sets, and machine-learned neural network modules". Information indicating a network structure, hyperparameters, and training data sets correspond to data for machine learning. Here, possible storage units (not illustrated) include, for example, magnetic recording media such as hard disks, and nonvolatile memory such as flash memory, and the like. Furthermore, the storage unit (not illustrated) may also be detachably attached to the medical information processing apparatus 100.

The information indicating a network structure according to the present embodiment is optional information indicating a network structure such as a neural network, for example. Information indicating a network structure includes, for example, data of optional formats enabling relationships between data to be expressed using a graph structure.

The hyperparameters according to the present embodiment are parameters for learning. To cite an example of a case where the information indicating a network structure is information indicating a neural network structure, such hyperparameters include, for example, the number of neurons, number of network layers and the learning rate, and the like. Note that the hyperparameters according to the present embodiment are not limited to or by the foregoing example and may, for example, be optional parameters enabling bandwidth to be allocated to the network indicated by the information indicating a network structure as a result of performing learning.

The training data sets according to the present embodiment are data sets including training data used for a plurality of learning processes. Training data includes, for example, data of optional formats corresponding to learning content, such as image data or text data, or the like.

Possible operating units (not illustrated) include an operating input device, described subsequently. Furthermore, possible display units (not illustrated) include a display device, described subsequently. Note that the medical information processing apparatus 100 need not comprise an operating unit (not illustrated) and/or a display unit (not illustrated).

[Example of Hardware Configuration of Medical Information Processing Apparatus 100]

Figure 15:
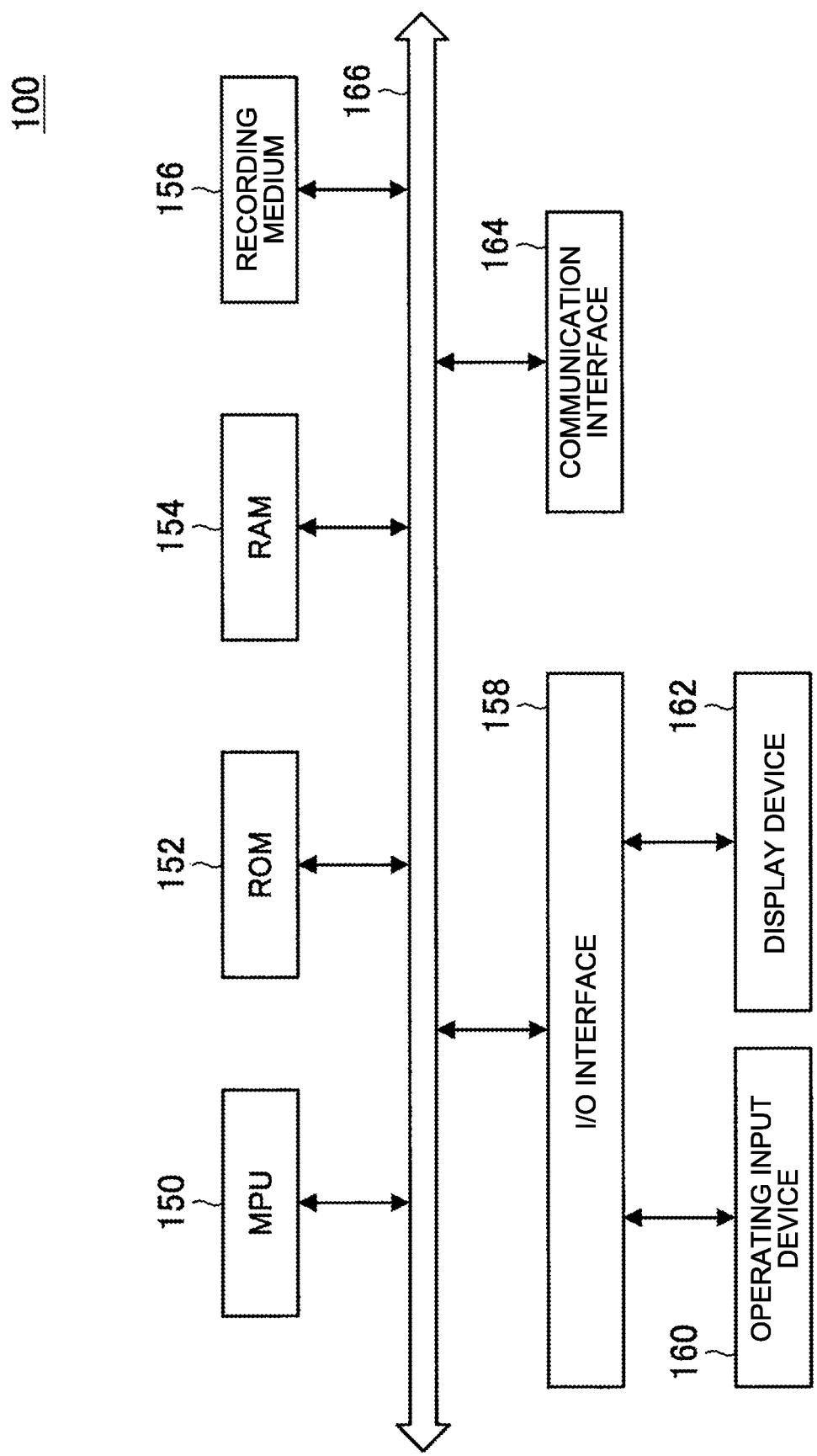
FIG. 15 is an explanatory drawing illustrating an example of a hardware configuration of the medical information processing apparatus according to the present embodiment.

FIG. 15 is an explanatory drawing illustrating an example of a hardware configuration of the medical information processing apparatus 100 according to the present embodiment. The medical information processing apparatus 100 comprises, for example, an MPU 150, a ROM 152, a RAM 154, a recording medium 156, an I/O interface 158, an operating input device 160, a display device 162, and a communication interface 164. Furthermore, the medical information processing apparatus 100 interconnects various components by a bus 166 constituting a data transmission path, for example. Further, the medical information processing apparatus 100 is driven by electrical power supplied from an internal power supply such as a battery which the medical information processing apparatus 100 comprises or by electrical power supplied from an external power supply connected thereto, for example.

The MPU 150 is configured from an arithmetic circuit such as an MPU or is configured from one, two, or more processors and various processing circuits, or the like, for example, and functions as the control unit 104, which controls the whole medical information processing apparatus 100. Furthermore, the MPU 150 fulfills the roles of a selection unit 110, an extraction unit 112, an editing processing unit 114, a display controller 116, and an arm controller 118, which are described subsequently, for example, in the medical information processing apparatus 100. Note that some or all of the selection unit 110, the extraction unit 112, the editing processing unit 114, the display controller 116, and the arm controller 118 may be configured from a dedicated (or a general-purpose) circuit (a processor, or the like, distinct from the MPU 150, for example).

The ROM 152 stores control data such as programs, calculation parameters, and the like, which are used by the MPU 150. The RAM 154 temporarily stores programs executed by the MPU 150, and the like, for example.

The recording medium 156 functions as a storage unit (not illustrated) and stores various data such as data pertaining to the information processing method according to the present embodiment, and various applications, for example. Here, examples of the recording medium 156 include magnetic recording media such as hard disks, and nonvolatile memory such as flash memory, and the like, for example. Furthermore, the recording medium 156 may also be detachably attached to the medical information processing apparatus 100.

The I/O interface 158 connects the operating input device 160 and the display device 162, for example. The operating input device 160 functions as an operating unit (not illustrated), and the display device 162 functions as a display unit (not illustrated). Here, examples of the I/O interface 158 include a universal serial bus (USB) terminal, a DVI terminal, a high-definition multimedia interface (HDMI) (registered trademark) terminal, and various processing circuits, or the like, for example.

Furthermore, the operating input device 160 is provided on the medical information processing apparatus 100 and is connected to the I/O interface 158 inside the medical information processing apparatus 100, for example. Examples of the operating input device 160 include buttons, direction keys, rotating selectors such as a jog dial, or a combination thereof, for example.

Furthermore, the display device 162 is provided on the medical information processing apparatus 100 and is connected to the I/O interface 158 inside the medical information processing apparatus 100, for example. Examples of the display device 162 include a liquid crystal display, an organic EL display, and the like, for example.

It goes without saying that the I/O interface 158 is also capable of connecting to external devices such as external operating input devices (a keyboard and a mouse, for example), or an external display device, of the medical information processing apparatus 100. Further, the display device 162 may also be a device that enables a display and user operations, such as a touch panel, for example.

The communication interface 164 is a communication means which the medical information processing apparatus 100 comprises, and functions as the communication unit 102 for performing communication wirelessly or via a cable with other devices constituting the medical information processing system 1000. Furthermore, the communication interface 164 is also capable of performing communication wirelessly or via a cable with other devices constituting the medical information processing system 1000. Here, examples of the communication interface 164 include, for example, a communication antenna and an RF circuit (wireless communication), an IEEE 802.15.1 port and a transceiver circuit (wireless communication), an IEEE 802.11 port and a transceiver circuit (wireless communication), or a LAN terminal and a transceiver circuit (wired communication), or the like.

The medical information processing apparatus 100 performs the foregoing processing pertaining to the information processing method according to the present embodiment by the configuration illustrated in FIG. 15, for example. Note that the hardware configuration of the medical information processing apparatus 100 according to the present embodiment is not limited to or by the configuration illustrated in FIG. 15.

For example, the medical information processing apparatus 100 need not comprise the communication interface 164 in cases where communication with an external device or the like is performed via a connected external communication device. In addition, the communication interface 164 may have a configuration that enables communication with one, two, or more external devices, or the like, by a plurality of communication systems.

Furthermore, the medical information processing apparatus 100 may have a configuration that does not include all or part of the recording medium 156, the operating input device 160, and the display device 162, for example.

In addition, the medical information processing apparatus 100 may have a configuration that corresponds to an application example of the medical information processing apparatus 100 which is described subsequently, for example.

Further, all or part of the configuration illustrated in FIG. 15 (or of configurations pertaining to modification examples) may be realized by one, two, or more integrated circuits (IC), for example.

An example of the configuration of the medical information processing apparatus 100 will be described by referring once again to FIG. 14. The communication unit 102 is a communication means which the medical information processing apparatus 100 comprises and performs communication wirelessly or via a cable with other devices constituting the medical information processing system 1000. Furthermore, the communication unit 102 is also capable of performing communication wirelessly or via a cable with devices other than devices constituting the medical information processing system 1000. The communication of the communication unit 102 is controlled by the control unit 104, for example.

Here, examples of the communication unit 102 include a communication antenna and an RF circuit, or a LAN terminal and a transceiver circuit, or the like, for example, but the configuration of the communication unit 102 is not limited to the foregoing. For example, the communication unit 102 may have a configuration corresponding to an optional standard that enables communication to be performed, such as a USB terminal and a transceiver circuit. In addition, the communication unit 102 may have a configuration that enables communication with one, two, or more external devices, or the like, by a plurality of communication systems.

The control unit 104 is configured from an MPU and fulfills the role of controlling the whole medical information processing apparatus 100, for example. Furthermore, the control unit 104 includes the selection unit 110, the extraction unit 112, the editing processing unit 114, the display controller 116, and the arm controller 118, for example, and plays a major role in executing the processing pertaining to the information processing method according to the present embodiment.

The selection unit 110 plays a major role in the processing (selection processing) of (1) above and selects target data corresponding to the selection condition from the candidate data. The selection unit 110 selects target data corresponding to a set selection condition each time a selection condition is selected manually via an operation, or the like, with respect to the operating unit (not illustrated) and/or whenever a selection condition is set based on surgery data acquired during surgery, for example. Note that, when a selection condition has been set, the selection unit 110 need not select target data in cases where the set selection condition is unchanged.

The extraction unit 112 plays a major role in the processing (extraction processing) of (2) above, detects a feature from among the target data selected by the selection unit 110, and extracts, from the target data, feature data corresponding to the detected feature. The extraction unit 112 extracts feature data whenever target data is selected by the selection unit 110. The extraction unit 112 extracts the feature data by machine learning such as deep learning, for example.

The extraction unit 112 extracts at least medical images as feature data, for example. Note that, if medical images are not included in the target data selected by the selection unit 110 or if there is no target data corresponding to the detected feature, the extraction unit 112 is capable of extracting feature data other than medical images.

The editing processing unit 114 plays a major role in the processing (editing processing) of (3) above and edits the feature data extracted by the extraction unit 112. Examples of editing processing include the processing indicated in D1 to D5 illustrated in FIG. 2 and the processing (including modification examples) described with reference to FIGS. 3 to 5, for example.

The display controller 116 plays a major role in the processing (display control processing) of (4) above and causes a display screen to display medical images corresponding to the surgery data acquired during surgery. Examples of editing processing include the processing (including modification examples) described with reference to FIG. 6, for example.

The arm controller 118 plays a major role in the processing (arm control processing) of (5) above and controls the action of an arm capable of carrying a medical instrument. As described earlier, the arm controlled by the arm controller 118 may be an arm which an external device such as the arm device 200 comprises or may be an arm which the medical information processing apparatus 100 comprises (if the medical information processing apparatus 100 functions as an arm device).

The arm controller 118 controls the action of the arm by specifying the surgery progress status based on the feature data corresponding to the surgery data acquired during surgery, for example. Furthermore, the arm controller 118 is also capable of recognizing various operations such as an operation to an operating device or a voice-based operation and of controlling an arm action so as to support a recognized operation, for example.

The medical information processing apparatus 100 performs the processing pertaining to the information processing method according to the present embodiment by the configuration illustrated in FIG. 14, for example.

Note that the configuration of the medical information processing apparatus 100 is not limited to or by the example illustrated in FIG. 14.

For example, the medical information processing apparatus 100 may also provide some or all of the selection unit 110, the extraction unit 112, the editing processing unit 114, the display controller 116, and the arm controller 118 separately from the control unit 104 (realize in a separate processing circuit, for example).

Furthermore, the medical information processing apparatus 100 need not comprise the communication unit 102 in cases where communication is performed with an external device via an external communication device that has the same functions and configuration as the communication unit 102, for example.

Furthermore, the medical information processing apparatus 100 need not include some or all of the editing processing unit 114, the display controller 116, and the arm controller 118, for example. Even if not provided with some or all of the editing processing unit 114, the display controller 116, and the arm controller 118, the medical information processing apparatus 100 is capable of performing the processing (selection processing) of (1) above and the processing (extraction processing) of (2) above. Even if not provided with some or all of the editing processing unit 114, the display controller 116, and the arm controller 118, the medical information processing apparatus 100 enable improvements in health worker convenience.

Note that, for the sake of expediency, the processing pertaining to the information processing method according to the present embodiment has been divided up into the foregoing processing (selection processing) of (1), the processing (extraction processing) of (2), the processing (editing processing) of (3), the processing (display control processing) of (4), and the processing (arm control processing) of (5). Thus, the configuration of the medical information processing apparatus 100 is not limited to the example illustrated in FIG. 14 and may have a configuration reflecting the division of the processing pertaining to the information processing method according to the present embodiment.

[II] Application Example of the Medical Information Processing Apparatus 100 According to the Present Embodiment Although the medical information processing apparatus 100 has been described by way of an example of the components of the medical information processing system according to the present embodiment, the present embodiment is not limited to or by such an embodiment. The medical information processing apparatus 100 may be applied to an optional device capable of performing the foregoing processing executed by the medical information processing apparatus 100 (the processing pertaining to the information processing method according to the present embodiment) such as a "personal computer (PC), a server, or another computer", a "tablet-type device", a "gaming device", or a "device comprising an arm capable of carrying a medical instrument, like the arm device 200", for example. Furthermore, with regard to the medical information processing system, another device constituting the medical information processing system such as the medical controller 10 may also function as the medical information processing apparatus 100. The medical information processing apparatus 100 may also be applied to an IC which can be integrated into a device like the foregoing, for example.

In addition, the medical information processing apparatus 100 according to the present embodiment may also be applied to a processing system premised on a connection to a network (or communication with each device) as in the case of cloud computing, or the like, for example). As an example of the foregoing processing system, a "system in which partial processing of the processing performed in the medical information processing apparatus 100 (processing pertaining to the information processing method according to the present embodiment) is performed by one device constituting the processing system, while processing other than this partial processing of the processing performed in the medical information processing apparatus 100 is performed by another device constituting the processing system", or the like, for example, may be used.

[III] Example of the Advantageous Effects Afforded by Using the Medical Information Processing Apparatus 100 According to the Present Embodiment The advantageous effects listed below, for example, are afforded as a result of using the medical information processing apparatus 100 according to the present embodiment. It goes without saying that the advantageous effects afforded by using the medical information processing apparatus 100 according to the present embodiment are not limited to the examples listed below.

It is possible to associate input data, from a camera and a microphone in a surgical setting, with time data which is synchronized with the input data, and manage, as one file system, various features (for example, "features automatically detected from the movement of people or equipment in a surgical setting, and the like", "features automatically detected from the movement of intraoperative treatment tools (forceps, scalpel, and the like) and from the instructions (voice) of a primary surgeon, and the like", and "features automatically detected from data which is input by a primary surgeon or an assistant, or the like, by using an input device, and the like").

Automatic editing, such as the cropping and stitching together of scenes before and after a point in time corresponding to a feature, is realized.

Automatically edited files can be edited manually based on the anatomical findings and the observations of a physician or the like, where the physician or the like manually adds text and/or images and so forth. Accordingly, the creation of a case-dependent surgical procedure protocol, for example, is straightforward.

By performing machine learning and the like of data which is categorized by patient information and by case, case types corresponding to patient attributes such as gender, age, and body type can be performed automatically.

In response to an increased number of cases, extracted scenes can be suitably added, substitution candidates can be presented, and automatic substitution may be performed.

A display of medical images on a display screen and/or sound outputs (a voice guide) can be realized based on extracted feature data or a protocol file created based on the feature data. Thus, intraoperative navigation assistance using a display of medical images on a display screen and/or sound outputs (a voice guide) is realized.

(Programs According to the Present Embodiment)

Programs (computer programs) for causing the computer system to function as the medical information processing apparatus 100 are executed by a processor or the like in the computer system, thereby enabling improvements in health worker convenience. A single computer or a plurality of computers may be used as the computer system according to the present embodiment. Serial processing pertaining to the information processing method according to the present embodiment is performed by the computer system according to the present embodiment.

The programs listed below, for example, may be used as the programs for causing the computer system to function as the medical information processing apparatus 100.

A program for causing the computer system to function as the "selection unit 110" and "extraction unit 112" which are illustrated in FIG. 14

A program for causing the computer system to function as the "selection unit 110", the "extraction unit 112", and "some or all of the editing processing unit 114, the display controller 116, and the arm controller 118" which are illustrated in FIG. 14

Moreover, programs for causing the computer system to function as the medical information processing apparatus 100 are executed by a processor or the like in the computer system, thereby enabling the foregoing advantageous effects afforded by the processing pertaining to the information processing method according to the present embodiment to be provided.

Preferred embodiments of the present disclosure have been described in detail hereinabove with reference to the accompanying drawings, but the technical scope of the present disclosure is not limited to or by such examples. It is obvious that a person ordinarily skilled in the art of the technical field of the present disclosure could arrive at various modification examples or revised examples within the scope of the technological ideas disclosed in the claims, and it is naturally understood that such examples belong to the technical scope of the present disclosure.

For example, although the provision of a program for causing a computer system to function as the medical information processing apparatus 100 according to the present embodiment has been indicated hereinabove, the present embodiment may provide the program together with a recording medium on which the program is stored.

The foregoing configurations illustrate an example of the present embodiment and naturally belong to the technical scope of the present disclosure.

Furthermore, the advantageous effects disclosed in the present specification are only descriptive or exemplary, and non-limiting. In other words, the technology according to the present disclosure affords, in addition to or instead of the foregoing advantageous effects, other advantageous effects which are obvious, based on the disclosure of the present specification, to a person skilled in the art.

Note that the following configurations also belong to the technical scope of the present disclosure.

(1) A medical information processing apparatus, including: a selection unit that selects, from candidate data including surgery data acquired during surgery, target data corresponding to selection conditions that include conditions relating to patient attributes, conditions relating to surgical-procedure types, and conditions relating to disease types; and an extraction unit that detects a feature from the selected target data and extracts feature data corresponding to the detected feature, from the target data, wherein the extraction unit extracts at least medical images as the feature data.

(2) The medical information processing apparatus according to (1), wherein the extraction unit extracts the feature data by machine learning.

(3) The medical information processing apparatus according to (2), wherein the machine learning is deep learning.

(4) The medical information processing apparatus according to any one of (1) to (3), wherein the target data includes a medical captured image captured by an imaging device during surgery, and wherein the medical image is the medical captured image.

(5) The medical information processing apparatus according to any one of (1) to (4), wherein the target data includes a medical illustration image, and wherein the medical image is a medical illustration image.

(6) The medical information processing apparatus according to any one of (1) to (5), wherein the target data includes sound collected by a sound collection device during surgery, and wherein the extraction unit also extracts sound as the feature data.

(7) The medical information processing apparatus according to any one of (1) to (6), wherein the target data includes text which is input by an operation to an operating device, and wherein the extraction unit also extracts text as the feature data.

(8) The medical information processing apparatus according to any one of (1) to (7), wherein the extraction unit detects a state-related feature and/or an action-related feature from the target data.

(9) The medical information processing apparatus according to (8), wherein the extraction unit detects, as the state-related feature, a point in time in the target data when a predetermined state is detected from the target data and detects, as the action-related feature, a point in time in the target data when a predetermined action is detected from the target data.

(10) The medical information processing apparatus according to any one of (1) to (9), further including an editing processing unit that edits the extracted feature data.

(11) The medical information processing apparatus according to (10), wherein the editing processing unit edits the feature data to generate protocol data for a case-related surgical procedure.

(12) The medical information processing apparatus according to any one of (1) to (11), further including a display controller that causes a display screen to display the medical images corresponding to the surgery data acquired during surgery.

(13) The medical information processing apparatus according to (12), wherein the selection unit selects the target data by setting the selection condition based on the surgery data acquired during surgery, and wherein the extraction unit extracts the medical images by detecting features from the selected target data and causes a display screen to display the medical images corresponding to the surgery data, among the extracted medical images.

(14) The medical information processing apparatus according to (13), wherein the extraction unit also issues notification regarding the grounds for extracting the medical images displayed on the display screen.

(15) The medical information processing apparatus according to claim (13) or (14), wherein the medical images corresponding to the surgery data and displayed on the display screen correspond to navigation images during surgery.

(16) The medical information processing apparatus according to any one of (1) to (15), including: an arm controller that controls the action of an arm capable of carrying a medical instrument, wherein the arm controller specifies a surgery progress status based on the feature data corresponding to the surgery data acquired during surgery and controls the action of the arm such that the medical instrument corresponding to the specified progress status is carried to a predetermined position corresponding to the specified progress status.

(17) An information processing method executed by a medical information processing apparatus, including the steps of: selecting, from among candidate data including surgery data acquired during surgery, target data corresponding to selection conditions that include a condition relating to a patient attribute, a condition relating to a surgical-procedure type, and a condition relating to a disease type; and detecting a feature from the selected target data and extracting, from the target data, feature data corresponding to the detected feature, wherein, in the extraction step, at least a medical image is extracted as the feature data.

In addition, the following configurations also belong to the technical scope of the present disclosure.

(1)
A medical information processing apparatus, including:
a selection unit that selects, from candidate data including surgery data acquired during surgery, target data corresponding to selection conditions that include conditions relating to patient attributes, conditions relating to surgical-procedure types, and conditions relating to disease types;
an extraction unit that detects a feature from the selected target data and extracts feature data corresponding to the detected feature, from the target data; and
an editing processing unit that edits the extracted feature data,
wherein the extraction unit extracts at least a medical image as the feature data.

(2)
The medical information processing apparatus according to (1), wherein the extraction unit extracts the feature data by using a model that has learned by machine learning.

(3)
The medical information processing apparatus according to (2), wherein the extraction unit learns the target data corresponding to the selection condition.

(4)

The medical information processing apparatus according to (2) or (3), wherein the machine learning is deep learning.

(5)

The medical information processing apparatus according to any one of (1) to (4), wherein the target data includes a medical captured image captured by an imaging device during surgery, and the medical image is the medical captured image.

(6)

The medical information processing apparatus according to any one of (1) to (5), wherein the target data includes a medical illustration image, and the medical image is a medical illustration image.

(7)

The medical information processing apparatus according to any one of (1) to (6), wherein the target data includes non-image data, and the extraction unit detects a feature from the non-image data.

(8)

The medical information processing apparatus according to any one of (1) to (7), wherein the target data includes sound collected by a sound collection device during surgery, and the extraction unit also extracts sound as the feature data.

(9)

The medical information processing apparatus according to any one of (1) to (8), wherein the target data includes text which is input by an operation to an operating device, and the extraction unit also extracts text as the feature data.

(10)

The medical information processing apparatus according to any one of (1) to (9), wherein the extraction unit detects a state-related feature and/or an action-related feature from the target data.

(11)

The medical information processing apparatus according to (10), wherein the extraction unit detects, as the state-related feature, a point in time in the target data when a predetermined state is detected from the target data and detects, as the action-related feature, a point in time in the target data when a predetermined action is detected from the target data.

(12)

The medical information processing apparatus according to any one of (1) to (11), wherein the editing processing unit edits the feature data to generate protocol data for a case-related surgical procedure.

(13)

The medical information processing apparatus according to (12), wherein the editing processing unit generates the protocol data for the surgical procedure from a plurality of cases.

(14)

The medical information processing apparatus according to any one of (1) to (13), further including: a display controller that causes a display screen to display the medical image corresponding to the surgery data acquired during surgery.

(15)

The medical information processing apparatus according to (14), wherein the selection unit selects the target data by setting the selection condition based on the surgery data acquired during surgery, and the extraction unit extracts medical images by detecting features from the selected target data and causes a display screen to display the medical image corresponding to the surgery data, among the extracted medical images.

(16)

The medical information processing apparatus according to (15), wherein the extraction unit also issues notification regarding the grounds for extracting the medical images displayed on the display screen.

(17)

The medical information processing apparatus according to (15) or (16), wherein the medical image corresponding to the surgery data and displayed on the display screen correspond to a navigation image during surgery.

(18)

The medical information processing apparatus according to any one of (1) to (17), including:

an arm controller that controls the action of an arm capable of carrying a medical instrument, wherein the arm controller specifies a surgery progress status based on the feature data corresponding to the surgery data acquired during surgery and controls the action of the arm such that the medical instrument corresponding to the specified progress status is carried to a predetermined position corresponding to the specified progress status.

(19)

An information processing method executed by a medical information processing apparatus, the method including the steps of:

selecting, from among candidate data including surgery data acquired during surgery, target data corresponding to selection conditions that include a condition relating to a patient attribute, a condition relating to a surgical-procedure type, and a condition relating to a disease type;

detecting a feature from the selected target data and extracting, from the target data, feature data corresponding to the detected feature; and editing the extracted feature data, wherein, in the step of extracting, at least a medical image is extracted as the feature data.

REFERENCE SIGNS LIST

100 MEDICAL INFORMATION PROCESSING APPARATUS
102 COMMUNICATION UNIT
104 CONTROL UNIT
110 SELECTION UNIT
112 EXTRACTION UNIT
114 EDITING PROCESSING UNIT
116 DISPLAY CONTROLLER
118 ARM CONTROLLER
200 ARM DEVICE
1000 MEDICAL INFORMATION PROCESSING SYSTEM
P1 EQUIPMENT STORAGE LOCATION
P1' ADDITIONAL EQUIPMENT STORAGE LOCATION
P2 EQUIPMENT INSTALLATION LOCATION
P3 EQUIPMENT DISPOSAL LOCATION

The invention claimed is:

1. A medical information processing system, comprising:
   training circuitry configured to:
      train a deep learning model on data corresponding to selection conditions that include conditions relating to patient attributes including at least one attribute different from a subject of a medical image, conditions relating to surgical-procedure types, and conditions relating to disease types; and
   processing circuitry configured to:
      select, from candidate data including surgery data acquired during surgery, target data corresponding to the selection conditions that include conditions relating to patient attributes including at least one attribute different from a subject of a medical image, conditions relating to surgical-procedure types, and conditions relating to disease types;
      detect a feature from the selected target data;
      extract feature data corresponding to the detected feature using the deep learning model, from the target data, the feature data including at least the medical image;
      edit the extracted feature data to generate protocol data for a case related surgical procedure based on previous operations and patients having similar attributes to a current patient;
      provide intraoperative navigation based on the protocol data; and
      monitor the surgery relative to the case related surgical procedure,
   wherein
   on condition that the surgery deviates from the case related surgical procedure to a modified surgical procedure, the processing circuitry is configured to
      extract feature data corresponding to the modified related surgical procedure,
      generate updated protocol data for the modified related surgical procedure,
      provide intraoperative navigation based on the updated protocol data, and
      feedback the updated protocol data to the training circuitry.

2. The medical information processing system according to claim 1, wherein
   the target data includes a medical captured image captured by an imaging device during surgery, and
   the medical image is the medical captured image.

3. The medical information processing system according to claim 1, wherein
   the target data includes a medical illustration image, and
   the medical image is a medical illustration image.

4. The medical information processing system according to claim 1, wherein
   the target data includes non-image data, and
   the processing circuitry is configured to detect a feature from the non-image data.

5. The medical information processing system according to claim 1, wherein
   the target data includes sound collected by a sound collection device during surgery, and
   the processing circuitry also extracts sound as the feature data.

6. The medical information processing system according to claim 1, wherein
   the target data includes text which is input by an operation to an operating device, and
   the processing circuitry also extracts text as the feature data.

7. The medical information processing system according to claim 1, wherein the processing circuitry is configured to detect a state-related feature and/or an action-related feature from the target data.

8. The medical information processing system according to claim 7, wherein
   the processing circuitry is configured to
   detect, as the state-related feature, a point in time in the target data when a predetermined state is detected from the target data, and
   detect, as the action-related feature, a point in time in the target data when a predetermined action is detected from the target data.

9. The medical information processing system according to claim 1, wherein the processing circuitry is configured to generate the protocol data for the surgical procedure from a plurality of cases.

10. The medical information processing system according to claim 1, wherein the processing circuitry is configured to cause a display to display the medical image corresponding to the surgery data acquired during surgery.

11. The medical information processing system according to claim 10, wherein
    the processing circuitry is configured to:
    select the target data by setting the selection condition based on the surgery data acquired during surgery,
    extract medical images by detecting features from the selected target data, and
    cause the display to display the medical image corresponding to the surgery data, among the extracted medical images.

12. The medical information processing system according to claim 11, wherein the processing circuitry is configured to issue a notification regarding the grounds for extracting the medical images displayed on the display.

13. The medical information processing system according to claim 11, wherein the medical image corresponding to the surgery data and displayed on the display correspond to a navigation image during surgery.

14. The medical information processing system according to claim 1, wherein the processing circuitry is configured to:
    control an arm capable of carrying a medical instrument,
    specify a surgery progress status based on the feature data corresponding to the surgery data acquired during surgery, and
    control the arm such that the medical instrument corresponding to the specified progress status is carried to a predetermined position corresponding to the specified progress status.

15. The medical information processing apparatus system according to claim 1, wherein the processing circuitry is configured to provide the interoperative navigation based on the updated protocol data includes displaying a medical image of a next scene that corresponds to the modified surgical procedure.

16. An information processing method executed by a medical information processing system, the method comprising:
    training a deep learning model on data corresponding to selection conditions that include a condition relating to patient attributes, wherein the patient attributes include at least one attribute independent of a subject, a condition relating to a surgical-procedure type, and a condition relating to a disease type;

selecting, from among candidate data including surgery data acquired during surgery, target data corresponding to selection conditions that include the condition relating to patient attributes, wherein the patient attributes include at least one attribute independent of a subject of a medical image, a condition relating to a surgical-procedure type, and a condition relating to a disease type;

detecting a feature from the selected target data and extracting, from the target data, feature data corresponding to the detected feature, the feature data including at least the medical image;

editing the extracted feature data using the deep learning model to generate protocol data for a case related surgical procedure based on previous operations and patients having similar attributes to a current patient;

providing intraoperative navigation based on the protocol data;

monitoring the surgery relative to the case related surgical procedure; and generating a modified surgical procedure, including extracting feature data corresponding to the modified surgical procedure deviating from the case related surgical procedure, generating updated protocol data for the modified surgical procedure, providing intraoperative navigation based on the updated protocol data, and feeding back the updated protocol data to the training.

17. The method as claimed in claim 16, wherein providing the interoperative navigation based on the updated protocol data includes displaying a medical image of a next scene that corresponds to the modified surgical procedure.

18. The method according to claim 16, further comprising:
controlling an arm capable of carrying a medical instrument,
specifying a surgery progress status based on the feature data corresponding to the surgery data acquired during surgery, and
controlling the arm such that the medical instrument corresponding to the specified progress status is carried to a predetermined position corresponding to the specified progress status.

19. The method according to claim 16, wherein
the target data includes non-image data, and
further comprising detecting a feature from the non-image data.

20. The method according to claim 16, wherein
the target data includes sound collected by a sound collection device during surgery, and
further comprising extracting sound as the feature data.

* * * * *